United States Patent
Mullaney et al.

(10) Patent No.: US 12,245,798 B2
(45) Date of Patent: Mar. 11, 2025

(54) BIDIRECTIONAL THERMALLY ACTUATED COMPONENT FOR USE IN MEDICAL DEVICES

(71) Applicant: TETRAVISION, LLC, Beacon, NY (US)

(72) Inventors: Michael W. Mullaney, Naples, FL (US); Daniel Moran, Beacon, NY (US)

(73) Assignee: TETRAVISION, LLC, Beacon, NY (US)

( * ) Notice: Subject to any disclaimer, the term of this patent is extended or adjusted under 35 U.S.C. 154(b) by 1059 days.

(21) Appl. No.: 17/176,732

(22) Filed: Feb. 16, 2021

(65) Prior Publication Data

US 2021/0259748 A1    Aug. 26, 2021

Related U.S. Application Data

(60) Provisional application No. 62/976,841, filed on Feb. 14, 2020.

(51) Int. Cl.
*A61B 17/72* (2006.01)
*A61B 17/00* (2006.01)

(52) U.S. Cl.
CPC .... *A61B 17/72* (2013.01); *A61B 2017/00137* (2013.01); *A61B 2017/00415* (2013.01)

(58) Field of Classification Search
CPC ...... B25J 9/142; A61B 17/72; A61B 17/7225; A61B 2090/064
See application file for complete search history.

(56) References Cited

U.S. PATENT DOCUMENTS

| | | | |
|---|---|---|---|
| 10,072,677 B2 * | 9/2018 | Bachmaier | F04B 17/03 |
| 10,330,125 B2 * | 6/2019 | Bachmaier | F15B 1/26 |
| 10,690,154 B2 * | 6/2020 | Zöls | F15B 11/022 |
| 2013/0263800 A1 | 10/2013 | Lee et al. | |
| 2015/0377222 A1 | 12/2015 | Hallila et al. | |
| 2019/0368515 A1 * | 12/2019 | Bachmaier | F15B 9/09 |

FOREIGN PATENT DOCUMENTS

| | | |
|---|---|---|
| GB | 1225102 A | 3/1971 |
| GB | 1503164 A | 3/1978 |

OTHER PUBLICATIONS

International Search Report and Written Opinion dated Jun. 24, 2021 from International PCT Appln. PCT/US2021/018201.

\* cited by examiner

*Primary Examiner* — Abiy Teka
(74) *Attorney, Agent, or Firm* — Amster, Rothstein & Ebenstein LLP

(57) ABSTRACT

A bidirectional thermally actuated component includes a heating element and wax material provided in an enclosed housing wherein the heating element is activated to melt the wax which expands to cause movement of the housing or an element mounted therein. When the heating element is deactivated, the was hardens and constricts to allow for movement in the opposite direction based on application of a force in the opposite direction, which may be provided by a biasing spring or a second actuator. An adjustable medical device may include the thermally actuated component to control adjustment of the device.

25 Claims, 22 Drawing Sheets

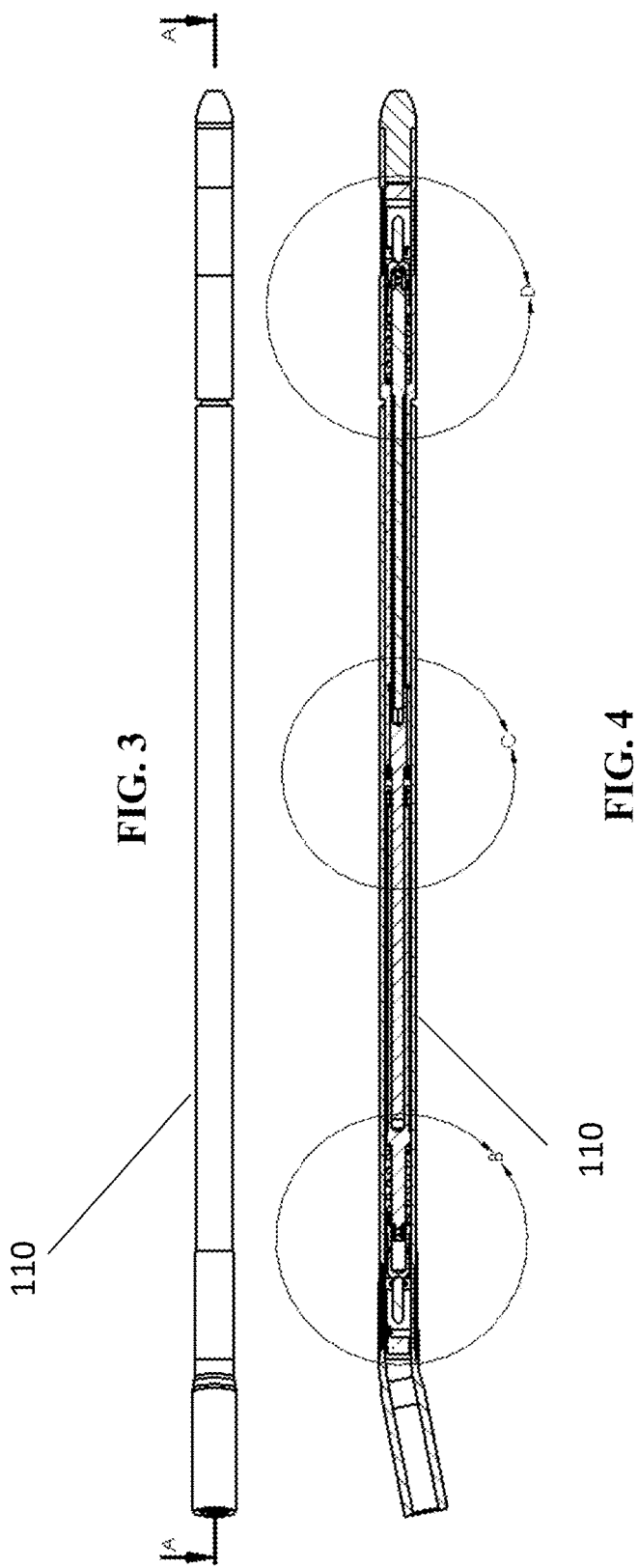

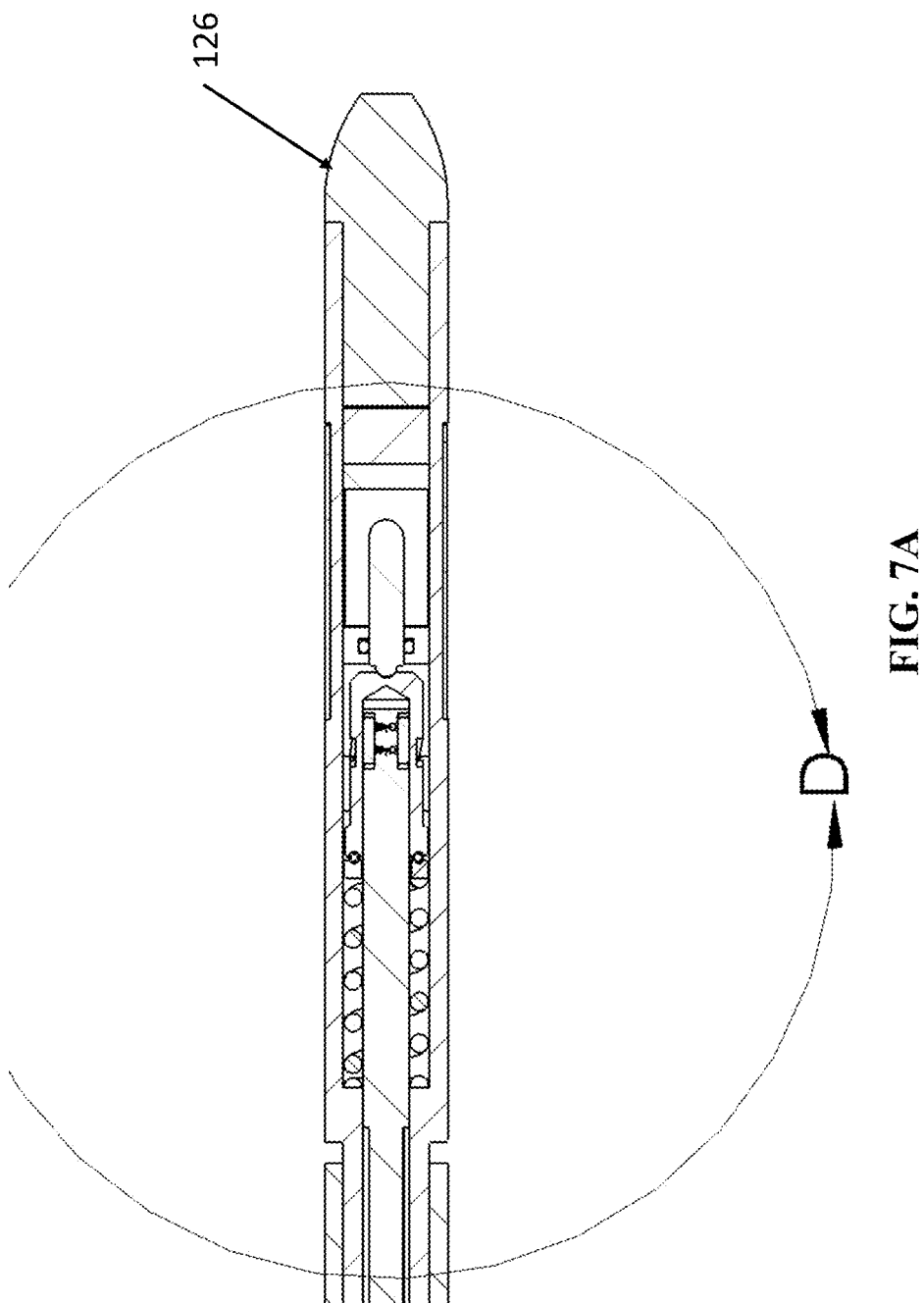

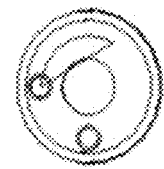
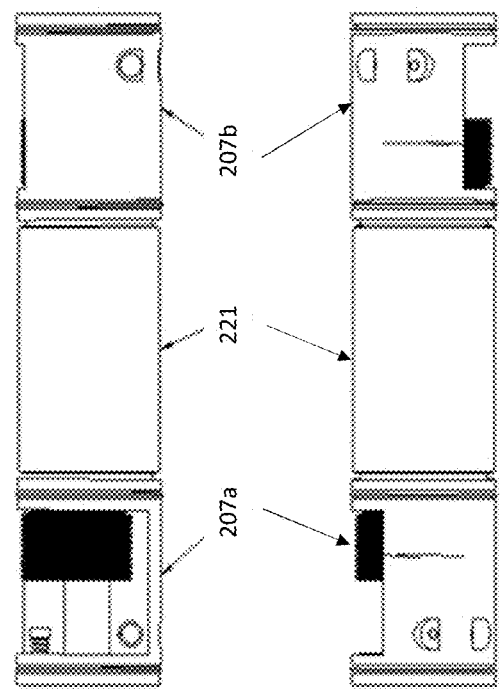
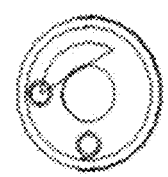
FIG. 13

BIDIRECTIONAL THERMALLY ACTUATED COMPONENT FOR USE IN MEDICAL DEVICES

CROSS-REFERENCE TO RELATED APPLICATIONS

The present application claims benefit of and priority to U.S. Provisional Patent Application Ser. No. 62/976,841 filed Feb. 14, 2020 and entitled BIDIRECTIONAL THERMALLY ACTUATED COMPONENT FOR USE IN MEDICAL DEVICES, the entire content of which is hereby incorporated by reference herein.

BACKGROUND

Field of the Disclosure

The present invention relates to a bidirectional thermally actuated component for use with a medical device. More specifically, the present invention relates to an actuator component that is activated by application or generation of heat in order to expand or contract in a predictable manner to provide for adjustment of medical equipment. While the component is preferably used in medical equipment it may be used in other applications as well.

Related Art

There are a variety of medical devices and equipment that are used to drive, correct, or maintain alignment in a direction and/or to provide compression and/or traction for a patient. Many conventional devices are limited to manually actuated adjustment elements, such as a rotating turnbuckle, and the like. Some devices use electric motors and gears that are powered by batteries to maintain alignment or to provide compression and traction. These powered devices are typically complex and costly. In addition, these devices are susceptible to error, including runaway catastrophic error. In some cases, the user may provide the wrong input, or an incomplete input, which may result in incorrect operation. In some cases, motors or gears may fail or malfunction. Even where a user enters a correct input, the device may not accept it or fail to provide the correct output. In some cases, the device may not perform at all, while in others, it may overperform. Motors may continue to run (or fail to run) with relative unlimited travel range, which may result in detrimental effects on the user. Indeed, errors may not be identified until the user's next doctor visit, either by direct visualization by the doctor or a series of x-rays to assess if everything is proceeding according to plan.

Where a human driven manipulator is used, the user may forget to perform a required input or perform an incorrect input. These type errors are often only discovered at the next doctor visit as well.

Accordingly, it would be desirable to provide an actuator component for use with a medical device, and a medical device using such an actuator, or other applications, that resolves these and other problems.

SUMMARY

It is an object of this invention to provide a bidirectional thermally actuated component that is safe and has a limited output relative to input. In embodiments, the output of the component is finite and therefore eliminates potential for gross or possibly catastrophic error.

In embodiments, the bidirectional thermally actuated component may use a material that transitions between solid and fluid based on temperature and may be as harmless as crayon material or paraffin wax, to name a few.

In embodiments, the bidirectional thermally actuated component is safe and may communicate data in order to confirm that a given input resulted in a correct output. In embodiments, the data may be shared with a doctor or other medical professional via the Internet, or other communication system or network in order to facilitate remote monitoring of patients, which may reduce the need for and cost of multiple visits and x-rays and allow for adjustments.

A thermally actuated component in accordance with an embodiment of the present disclosure includes: a flexible container element expandable in a first direction into an expanded position and biased to return to a retracted position; a thermally responsive material stored in the flexible container; a heating element positioned such that heat from the heating element melts the thermally responsive material when the heating element is activated such that the flexible container expands into the expanded position and the thermally responsive material compresses as it cools when the heating element is deactivated such that the flexible container returns to the retracted position.

In embodiments, the thermally responsive material is a eutectic wax.

In embodiments, the flexible container includes at least a first opening formed therein.

In embodiments, the first opening is configured to receive at least a portion of the first heating element.

In embodiments, the thermally actuated component includes a plug positioned in the first opening to keep the thermally responsive material in the flexible container.

In embodiments, the plug further includes a passage formed therein and configured to receive the heating element.

In embodiments, the thermally actuated component includes at least one power source operatively connected to the heating element to selectively activate the heating element such that the flexible container expands and contracts.

In embodiments, the power source is an inductive power source.

An intermedullary lengthening nail in accordance with an embodiment of the present disclosure includes: a hollow body; a shaft extending through the hollow body and slidable in the hollow body; a tension rod engaged in the shaft; a bidirectional pump mounted in the hollow body between a first cavity with a first volume and a second cavity with a second volume, wherein the first cavity is provided between the bidirectional pump and the shaft and the second cavity is position between the bidirectional pump and a piston, and the first cavity and second cavity include liquid; control circuitry operably connected to the bidirectional pump and configured to control operation of the pump; wherein the control circuitry controls the pump to move fluid from the first cavity into the second cavity to retract the piston, and the control circuitry controls the pump to move the fluid from the second cavity to the first cavity to extend the tension rod and the shaft.

In embodiments, the bidirectional pump includes: a first thermally actuated component positioned to move fluid from the first cavity to the second cavity; a second thermally actuated component positioned to move fluid from the second cavity to the first cavity; and an intermediate section positioned between the first thermally actuated component and the second thermally actuated component.

In embodiments, the intermedullary lengthening nail includes a first coil positioned around the intermediate section and electrically connected to the control circuitry and the bidirectional pump to provide power to at least the control circuitry and the bidirectional pump.

In embodiments, the control circuitry is provided in the intermediary section.

In embodiments, the control circuitry is mounted in a potting material to provide water resistance.

In embodiments, the first thermally actuated component includes: a first flexible container element expandable in a first direction into an expanded position and biased to return to a retracted position; a first thermally responsive material stored in the flexible container; a first heating element positioned such that heat from the first heating element melts the thermally responsive material when the first heating element is activated such that the first flexible container expands into the expanded position and the thermally responsive material compresses as it cools when the first heating element is deactivated such that the first flexible container returns to the retracted position, wherein expansion and contraction of the first flexible container is used to pump the fluid from the first cavity to the second cavity.

In embodiments, the first heating element is operably connected to the control circuitry and selectively activated by the control circuitry to expand and contract the first flexible container.

In embodiments, the first heating element is electrically connected to the coil and selectively activated when current is induced in the coil.

In embodiments, the second thermally actuated component includes: a second flexible container element expandable in a first direction into an expanded position and biased to return to a retracted position; a second thermally responsive material stored in the flexible container; a second heating element positioned such that heat from the second heating element melts the thermally responsive material when the second heating element is activated such that the second flexible container expands into the expanded position and the thermally responsive material compresses as it cools when the second heating element is deactivated such that the second flexible container returns to the retracted position, wherein expansion and contraction of the second flexible container is used to pump the fluid from the second cavity to the first cavity.

In embodiments, the second heating element is operably connected to the control circuitry and selectively activated by the control circuitry to expand and contract the second flexible container.

In embodiments, the second heating element is electrically connected to the coil and selectively activated to expand and contract the second flexible container when current is induced in the coil.

In embodiments, the intermedullary lengthening nail includes a third cavity provided in the intermediary section and in fluid communication with the bidirectional pump and the first cavity and the second cavity such that fluid moving between the first cavity and the second cavity and fluid moving from the second cavity to the first cavity may be temporarily stored therein.

An intermedullary lengthening nail in accordance with an embodiment of the present disclosure includes: a body; a power source mounted in the body; control circuitry mounted in the body and electrically connected to the power source; a first bulkhead positioned between the control circuitry and a first open space in the body; a second bulkhead spaced away from the first bulkhead in a direction opposite the control circuitry; eutectic wax positioned between the first bulkhead and the second bulkhead; a piston mounted in the eutectic wax and extending through the second bulkhead, the piston movably mounted to extend and retract through the second bulkhead; a heating element electrically connected to the control circuitry such that the heating element is selectively activated by the control circuitry and positioned such that heat from the heating element melts the wax such that the piston extends, wherein the piston is biased into a retracted position such that it returns to the retracted position when the heating element is deactivated and the eutectic wax hardens; and an extension rod operatively connected to the piston such that the expansion of the piston extends the extension rod.

In embodiments, the extension rod is operatively connected to the piston such that retraction of the piston retracts the extension rod.

In embodiments, the power source is an induction coil wrapped around the body.

BRIEF DESCRIPTION OF THE DRAWINGS

The above and related objects, features and advantages of the present disclosure will be more fully understood by reference to the following detailed description of the preferred, albeit illustrative, embodiments of the present invention when taken in conjunction with the accompanying figures, wherein:

FIG. 3 illustrates an exemplary intermedullary lengthening nail suitable for use with a bidirectional thermally actuated component in accordance with another embodiment of the present application;

FIG. 4 illustrates a cross-sectional view of the intermedullary lengthening nail of FIG. 3 in accordance with an embodiment of the present application;

FIG. 7A illustrates and extended view of the detailed view provided in FIG. 7;

FIG. 13 is more detailed view of the bidirectional pump of FIG. 12;

DETAILED DESCRIPTION OF THE EXEMPLARY EMBODIMENTS

In embodiments, a medical device using a bidirectional thermally actuated actuator component may be implemented in at least two embodiments. In a first embodiment, the medical device may include a thermally actuated bidirectional actuator component that utilizes a hydraulic approach in which motion and structural support may be provided utilizing a working fluid that is selectively transferred between two sides of a piston assembly via expansion of the thermal actuator and the resultant change in pressure. In another embodiment, the device may use a thermally actuated actuator component with a mechanical approach in which a mechanism transforms linear motion and force generated by expansion and retraction of a thermal actuator component into rotational motion to actuate a screw. In embodiments, the rotational motion may be used to rotate a jack screw. In both embodiments, captured eutectic wax may be used in either a bellows structure, a bladder or in any enclosed volume in combination with a piston.

Figure 1:
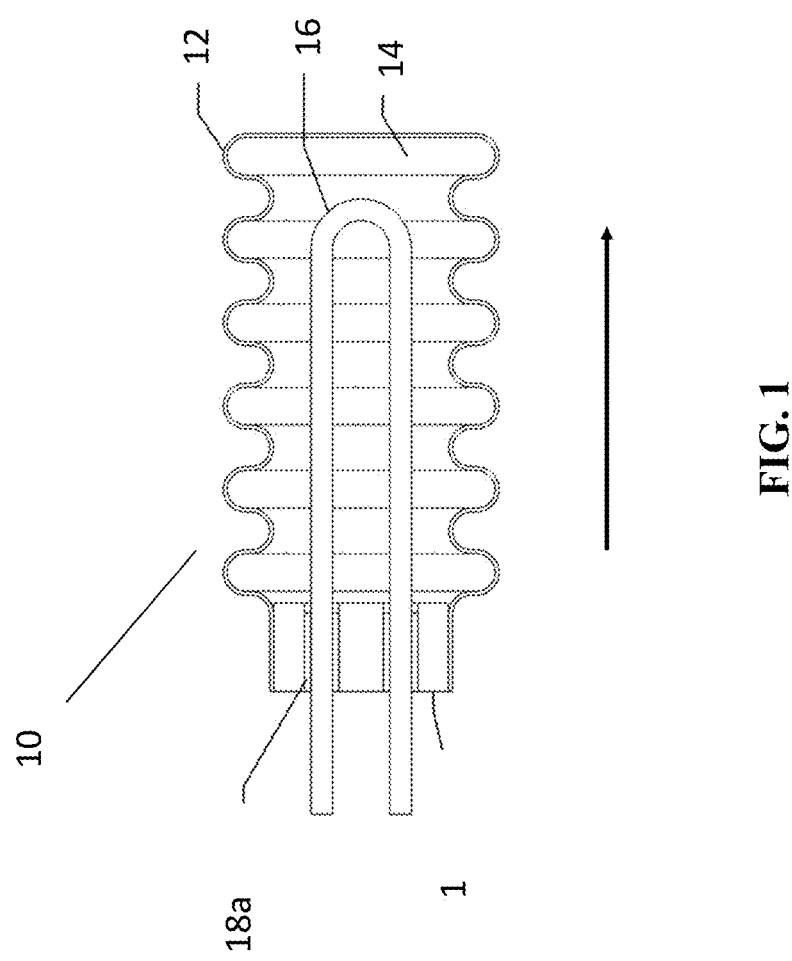
FIG. 1 illustrates an exemplary cross-sectional view of a bidirectional thermally actuated component in accordance with an embodiment of the present application.

FIG. 1 illustrates a cross-sectional view of an exemplary bidirectional thermally actuated actuator component 10. In embodiments, the bidirectional thermally actuated actuator component 10 may include a metallic bellows structure 12 in which a wax material 14 is received and stored. In embodiments, an electric heating element 16 may also be provided in the metallic bellows structure 12 and in contact with the wax material 14. In embodiments, the electric heating element 16 may be provided adjacent to the wax material but not in contact therewith such heating from the heating element melts the wax material 14. While the term metallic bellows is used, in embodiments, the bellows structure 16 need not be metallic. In embodiments, the bellows structure 12 may be a flexible and expandable bladder. In embodiments, the bellows structure 12 may be any suitable container that is expandable and resilient to return to its prior state after expansion.

In embodiments, the heating element 16 may be a resistive heating element. In embodiments, a plug 18 may be provided at a base of the metallic bellows structure 12 to keep the wax material 14 inside the bellows structure. In embodiments, the plug 18 may include an opening to provide access into the bellows structure 12 to allow the heating element 16 to pass through into the interior of the bellows structure 12. In embodiments, a seal 18a may be provided around the opening in the plug 18 to allow the heating element 16 to pass through while preventing leakage of wax. In embodiments, the plug 18 may not be used and the heating element 16 may enter metallic bellows structure 12 via an opening therethrough. In embodiments, the opening in the metallic bellows structure 12 may be configured to securely receive the heating element 16 to avoid leaks. In embodiments, the heating element 16 may be a ceramic or other type of heating element. In embodiments, the heating element 16 may be energized using a near field charger or other inductive power source. In embodiments, a near field charger operates on the principle of inductive coupling or electrical transformation. In embodiments, alternating current may be applied to a primary coil (not shown) placed in close proximity to a secondary coil.

In embodiments, the primary coil may be positioned external to the user's body while the secondary coil may be positioned within an implant including the actuator component 10 in the user's body. In embodiments, the secondary coil may be integrated into the actuator component 10. In embodiments, the secondary coil may be or may be electrically connected to the heating element 16 to provide power to activate the heating element. In embodiments, the bidirectional thermally actuated actuator component 10 may be included in an implant positioned in the user's body to provide for adjustment thereof. In embodiments, positioning of the primary coil may be based on the location of the implant in the user's body to ensure that a current is induced in the secondary coil which may be used to activate the implant and the thermally actuated actuator component 10. In embodiments, orientation of the primary and secondary coil may be optimized to maximize the inductive coupling based on the position of the implant in the user's body. In embodiments, both the primary and secondary coil may be coaxially stacked much like a cell phone charging pad. In embodiments, the primary and secondary coils may be placed in a parallel orientation. In either case, magnetic material may be used to focus the magnetic flux dependent on the location within the body where the implant is placed. In embodiments, the heating element 16 may be electrically connected to one or more other electric power supplies, such as a battery or capacitor, to name a few. In embodiments, a wired electrical connection may be provided, for example to an AC line voltage. In embodiments, the power source may include a transformer to provide an appropriate voltage suitable for use with the heating element 16. In embodiments, the heating element 16 may be connected to a processor, microprocessor or other control device or control circuitry which may be used to activate and deactivate the heating element. In embodiments, the heating element 16 is preferably selectively activated and deactivated in order to activate the actuator component 10.

Figure 21B:
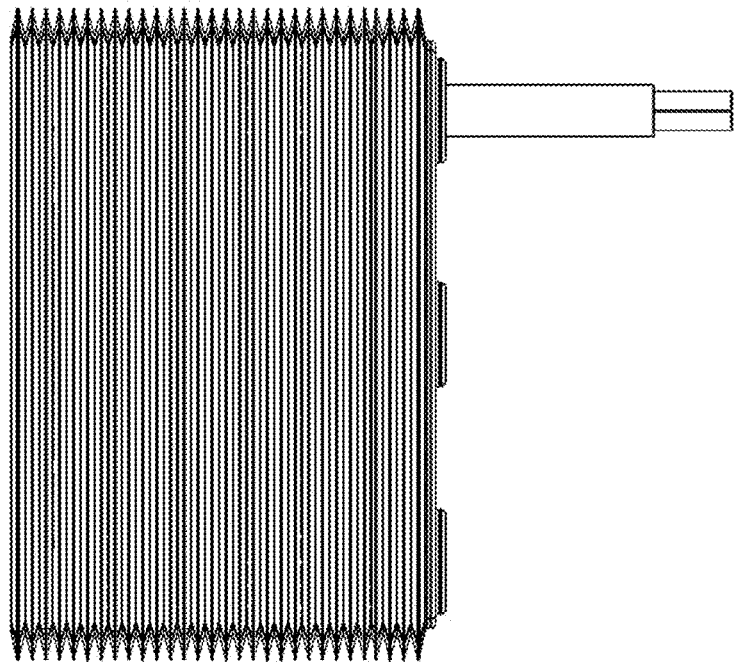
FIG. 21B illustrated an exemplary embodiment, of a bellows structure in a retracted state.
Figure 21A:
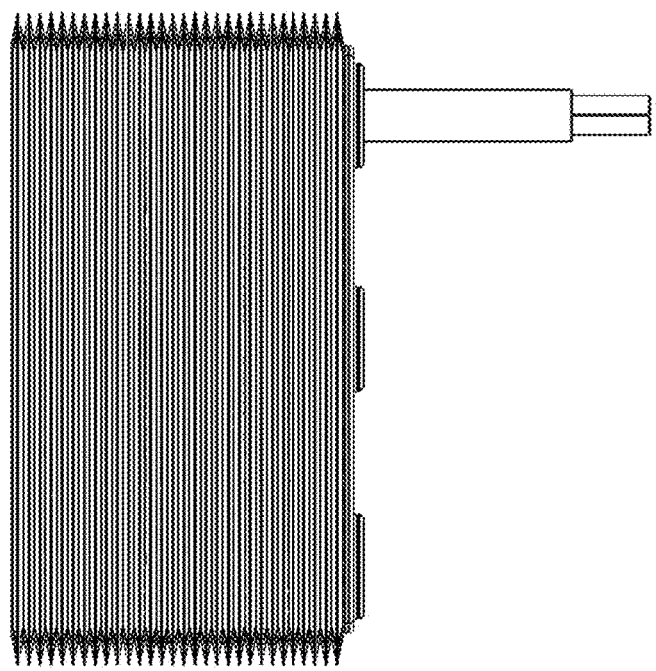
FIG. 21A illustrates an exemplary embodiment, of a bellows structure in an extended state.

In embodiments, the metallic bellows structure 12 may be configured to allow for expansion in a linear direction, as indicated by the arrow in FIG. 1, for example. In operation, when an electric current is induced or otherwise provided in the heating element 16, the heat from the heating element 16 melts the wax material 14 which expands to move the metallic bellows structure 12 in the direction of the arrow in FIG. 1. FIG. 21A provides an exemplary illustration of a metallic the bellows structure 12 in a retracted position while FIG. 21B illustrates the metallic bellows structure in an extended position. When power is turned off, the heating element 16 and wax material cools and the wax material constricts as it hardens and the bellows structure 12 retracts in the opposite direction of the arrow to its original state. In embodiments, the metallic bellows structure 12 may be biased into the retracted state such that once the wax material hardens, the bellows structure will return to the retract state or substantially to the retracted state. In embodiments, the metallic bellows 12 is resilient and has a spring rate that is sufficient to allow for the bellows to return to its original, retracted state after the wax hardens. In embodiments, while a higher spring rate may provide for a quicker return of the bellows structure 12 to its retracted state, however, a higher spring rate also may require additional pressure to provide for expansion of the bellows. In embodiments, it is preferable to minimize the amount of pressure needed for expansion. In embodiments, the spring rate of the bellows 12 may vary depending on the application in which it is used. In embodiments, where both the expansion and the retraction in a reciprocating fashion is used, the spring rate may be set such that the net output force is equal in both phases. In one example where a wax actuator is use to provide 100 lbF based on volumetric expansion, in embodiments, the spring force of the bellows 12 may have an initial spring load of 50 lbF with zero rate so that at full extension there would still be 50 lbF of initial spring load and 50 lbF of available actuator output. In embodiments, upon retraction there would be 50 lbF of spring load to work with all the way back to full retraction. In embodiments, the initial spring load and rate may be tailored to maximize the available work in relation to the required work keeping and the balance of force vs distance vs direction may be highly dependent on both the clinical application and design choices.

Figure 2:
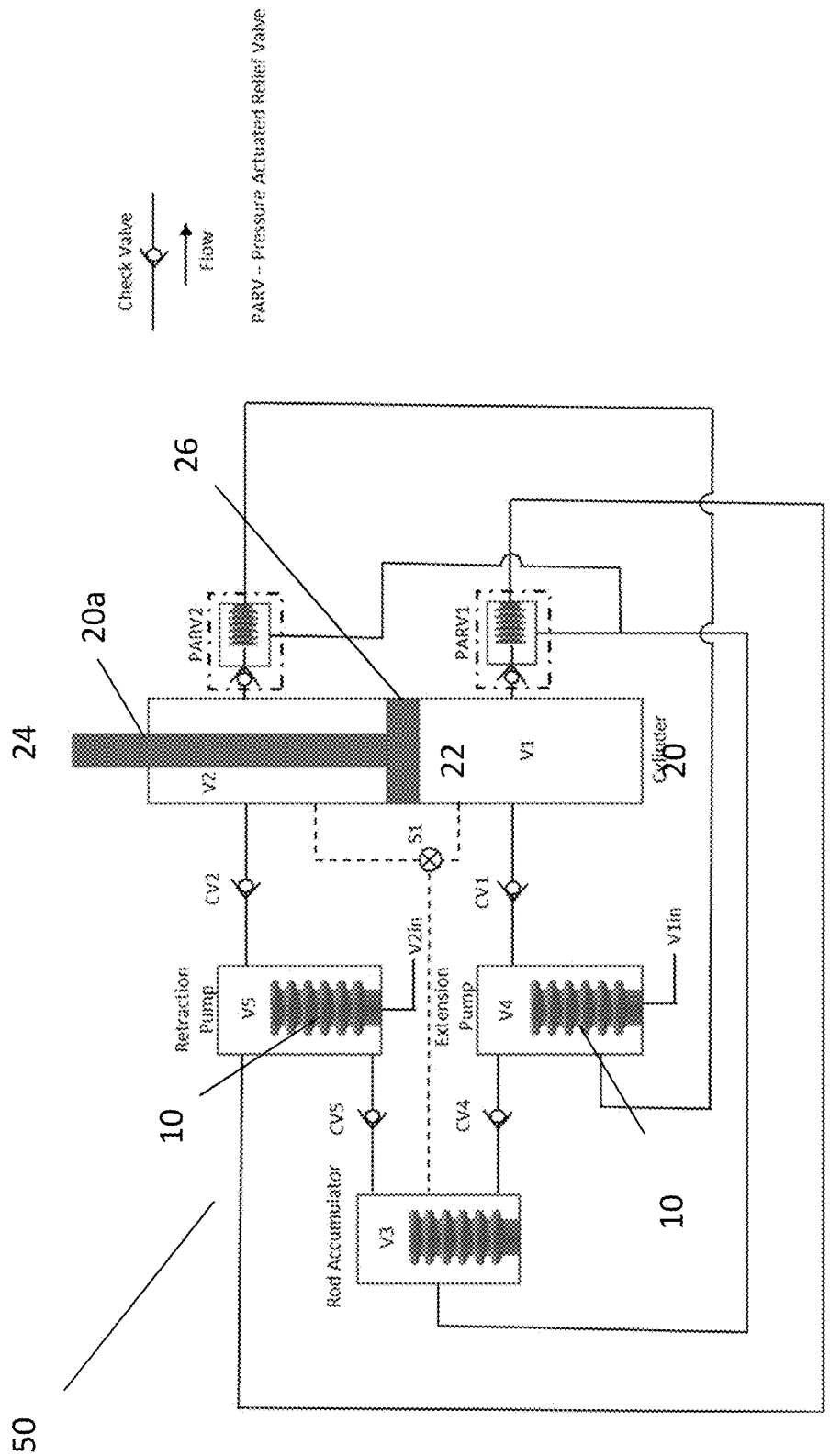
FIG. 2 illustrates a hydraulic pressure system using the bidirectional thermally actuated component of FIG. 1 in accordance with an embodiment of the present application.

In embodiments, cyclical heating (expansion) and cooling (contraction) of the wax 14 in the bellows 12 of component 10 may be employed to provide a fluidic pump for use in a hydraulic system 50 as illustrated in FIG. 2. In embodiments, the component 10 may be used in conjunction with a hydraulic cylinder 20, as can be seen in FIG. 2, for example. In embodiments, the hydraulic cylinder 20 may include a piston 22 held within the closed cylinder 20. In embodiments, the piston 22 may be connected to a rod 24 that extends through one end of the closed cylinder 20 and extends and retracts as the piston moves in the cylinder. In embodiments, a dynamic seal 26 maybe provided around the periphery of the piston 22 and around the cylindrical opening 20a at the end of the cylinder 20 through which rod 24 exits to divide the cylinder 20 into two isolated volumes V1, V2. In embodiments, transferring fluid into one volume while removing it from the other volume will drive the piston 22 in one direction toward the volume of lower pressure along the axis of the cylinder 20. The first volume is denoted V1 and the second volume is denoted V2. The amount of working fluid in each of the first volume V1 and second volume V2 will increase or decrease as a function of piston translation, however, will do so at different rates because volume V1 is positioned on the swept area of the piston 22 and the second volume V2 is positioned in an area defined by the swept area of the piston 22 minus the area of the rod 24. The total volume V1+V2 will increase as the rod 24 is extended and will decrease as the rod is retracted.

In embodiments, a third connected variable volume V3 may be used. In embodiments, this third volume V3 may be referred to as the "rod accumulator" and may be constructed using a spring-loaded piston in a cylinder. In embodiments, the "rod accumulator" may be a flexible, sealed bellows containing a gas. In embodiments, the rod accumulator may be a bladder or a piston in a cylinder. In embodiments, the "rod accumulator" may be a passive device whose only function is to accommodate the differential volume change between V1 and V2 as the rod 24 extends and retracts. This differential volume is a result of the fact that the rod 24 has a cylindrical volume that must be considered as it extends and retracts from V2 whereas V1 does not have the same. In embodiments, to lock the rod 24 in a given position, the volumes V1, V2, and V3 may be isolated from each other forming 3 closed volumes. In embodiments, isolation of the volumes V1, V2, V3 may be accomplished using a simple shutoff valve S1. In embodiments, opening the valve S1 allows fluid to flow as needed to allow the rod 24 to be freely positioned.

In embodiments, in order for the rod 24 to effect motion by extending or retracting, two pumps maybe configured using actuators that use a wax material (such as paraffin wax or eutectic wax), which may be embodied by or include the component 10 of FIG. 1. In embodiments, the thermally actuated component 10 may be contained within each of the respective enclosed volumes V4 and V5. Check valves CV2 and CV5 are provided with respect to the volume V5. Check valves CV4 and CV1 and pressure activated release valve PARV2 are provided with respect to volume V4. In embodiments, these pumps are referred to as "extension pump" and "retraction pump."

In embodiments, extension of the piston 24 may be affected by the application of a voltage at the electrical input V1in. In embodiments, the voltage may be used to power the electric heater 16 discussed above, for example, causing wax to melt and resulting in expansion of the actuator 10 within volume V4 to expand, thereby increasing the pressure within volume V4. In embodiments, the voltage V1in may be used to power a controller or control circuitry that maybe use to control the heater 16 to control application of heat. Alternatively, a controller or control circuit nay be used to selectively provide the voltage V1 to the heater. In embodiments, the voltage V1in may be applied from a power source such as the an inductive coupling discussed above or any other suitable power source, such as a direct source of current. In embodiments, the check valve CV1 allows fluid to flow from V4 to V1 in the cylinder 20 when the pressure in V4 exceeds a predetermined value. In embodiments, the predetermined value will depend on external applied loads and the cross-sectional area of the actuator component 10 for the given apparatus or device that it is used in, for example, an implanted medical device. In embodiments, eutectic wax actuators such as the actuator component 10 may develop up to about 3000 psi of pressure during the expansion resulting from the melting process. In embodiments, when there aren't any significant loads applied, expansion will occur at lower pressures. In embodiments, at the same time, the increased pressure in V4 is applied to the pressure relief valve PARV2 allowing fluid to flow from volume V2 to volume V3. In embodiments, the increase of pressure in volume V1 as fluid flows from the volume V4 into volume V1, combined with the decrease in pressure in volume V2 as fluid flows from volume V2 to volume V3 allows the piston 22 to move upward and extend the rod 24. In embodiments, once the voltage V1in is removed, the heating element may be disengaged and the wax in the actuator 10 in the volume V4 begins to contract, lowering the pressure in volume V4 resulting in the check valve CV1 closing and the valve CV4 opening to allow fluid to flow from volume V3 into volume V4. Once the actuator 10 in volume V4 is completely contracted to its original state, the pressure in volume V4 may return to the value it had prior to the actuation cycle by taking up fluid from volume V3. In embodiments, the relative volumes of the volumes V1, V2, V3 and V4 may vary depending on the size of the component 10 and the implant that is it provided in as well as the amount of extension desired for a single expansion cycle.

In embodiments, retraction of the rod 24 may be affected by the application of voltage at electrical input V2in. This voltage may be provided via a power source such as the induction coil discussed above or otherwise. In embodiments, the voltage V2in may activate a heating element 16 in a second actuator component 10 in the volume V5. In embodiments, as noted above, the actuator component may be powered via a direct current. In embodiments, application of the voltage V2in causes the heating element 16 in the second actuator component 10 contained within volume V5 to heat the wax and expand the actuator to increase the pressure within volume V5. In embodiments, the check valve CV2 allows fluid to flow from volume V5 to volume V2 of the cylinder 20 when the pressure in volume V5 exceeds a certain value. In embodiments, the specific values are a function of the desired application and relief pressures would depend on the applied external loads. In embodiments, check valves may operate at very low differential pressures sufficient to eliminate the possibility of back flow. In embodiments, at the same time, the increased pressure in V5 is applied to the pressure actuated relief valve PARV1 allowing fluid to flow from volume V1 to volume V3. In embodiments, this increase of pressure in the volume V2 and decrease of pressure in the volume V1 causes the piston 22 to move down and retract the rod 24. In embodiments, once the voltage V2in is removed, the actuator component 10 within volume V5 begins to contract back to its original state, lowering the pressure in V5 causing the check valve CV2 to close and valve CV5 to open allowing fluid to flow from volume V3 into volume V5. In embodiments, once the actuator component 10 in volume V5 is completely contracted into its original state, the pressure in volume V5 returns to the value it had prior to the actuation cycle by taking up fluid from volume V3. The pressure in the various volumes may be a function of the applied external loads. The eutectic wax is preferably capable of generating pressures of upwards of 3000 psi which may be applied across a given desired cross-sectional area to support the externally applied loads.

In embodiments, either the expansion cycle or the retraction cycle described above may be repeated as many times as necessary to move the rod 24 to any incremental position. An advantage of this is that when such actuators are used in implants or corrective medical devices, each adjustment made is limited to the extension length of the rod 24 such that runaway or cataclysmic failures are unlikely. In embodiments, the size of the increment for each movement may be set based on restricting how much the component 10 expands. As noted above, in embodiments, the amount of expansion may vary. In embodiments, different sized or volume actuator components 10 may be used in different applications. In embodiments, volume may be dependent on the size of the component 10 and/or the implant or device in which it is used as well as the amount of extension desired for a single expansion cycle.

In embodiments, feedback regarding the rod position may be provided using a position or pressure sensor used to measure the state of the rod accumulator (volume V3 in FIG. 2) in the volume, since this will follow a predictable relationship with respect to rod extension. In embodiments, a simple position sensor, which may work on the same principle as a potentiometer where a linear strip of resistive material may be coupled to a sliding contact may be used. In embodiments, the resistance is a known function of contact position along the linear strip. In embodiments, for a pressure embodiment, the rod accumulator (volume V3 in FIG. 2, for example) may include a closed volume of a compressible gas, the pressure of which is a function of the volume of the closed volume. As this volume decreases, the pressure increases and vice versa. This relationship may be characterized in terms of rod extension such that a position of the rod may be determined based on the pressure in the rod accumulator. In embodiments, a pressure sensor may be placed within the closed volume of the rod accumulator. Such pressure sensors come in many different forms from strain gauge-based designs to piezoelectric elements. Different sensor types may be selected based on the particular application. In embodiments, a position or location sensor may be provided between the rod 24 and the cylinder 20 to determine the relative position of each, for example, using the resistive sensor mentioned above. In embodiments, where a load cell is used, the sensor may be placed in series between the cylinder wall, a spring and the rod. As the rod 24 moves, the length of the spring which results in a change in the spring force that is sensed by the load cell. A correlation between the load and travel may be established to measure relative position. In embodiments, the position information collected as noted above may be communicated to a doctor or other healthcare professional and used to confirm that the device using the hydraulic system 50, for example, is properly adjusted and providing the desired corrective force in the patient's body. That is, in embodiments, the hydraulic system 50 may be integrated into an implant 1000 (see FIG. 22, for example) or other medical device and implanted into a patient's body to provide corrective treatment.

Figure 22:
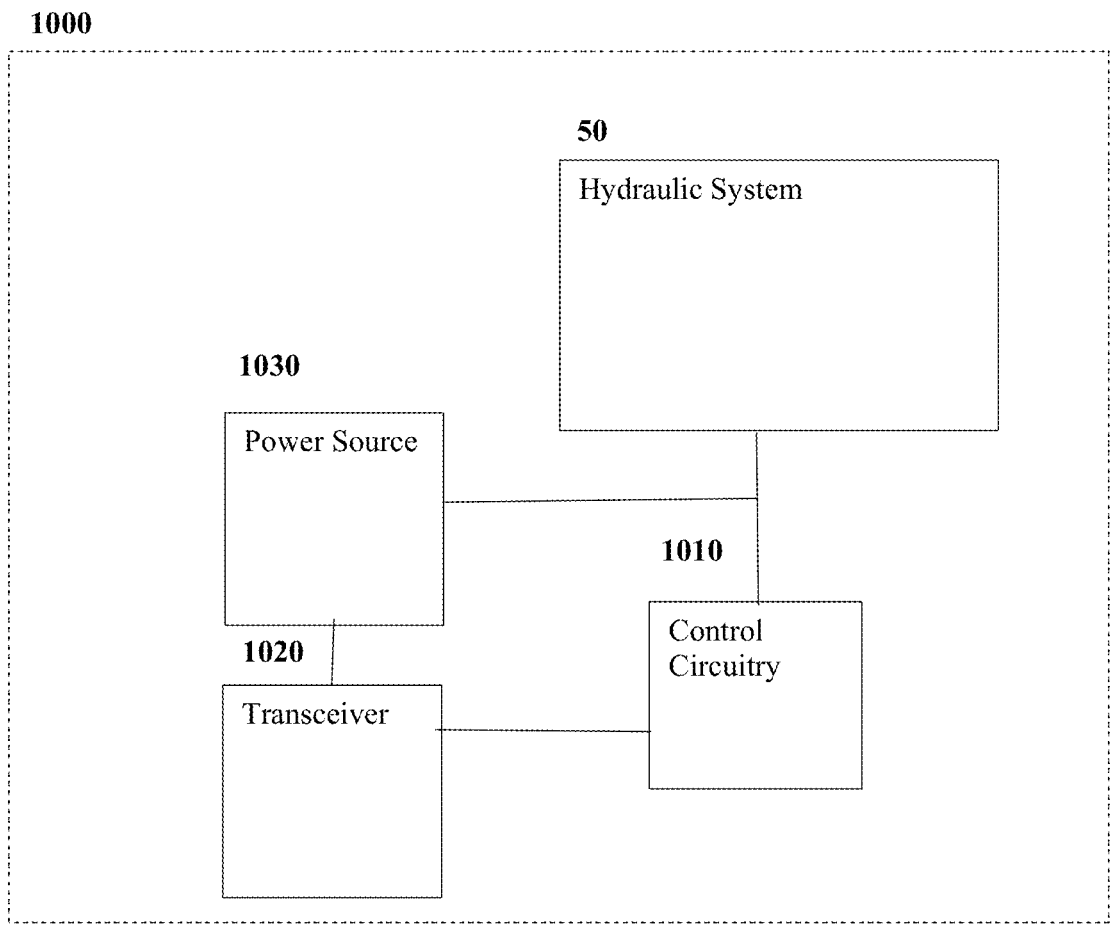
FIG. 22 illustrates an exemplary implant device that may include a thermally actuated element in accordance with an embodiment of the present disclosure.

In embodiments, the position information may be used to provide feedback that may be used to ensure that adjustments are being properly made. In embodiments, a control circuit or controller may be provided on or cooperatively connected to the implant 1000. FIG. 22 illustrates an exemplary block diagram of an implant 1000 that may incorporate a hydraulic pump system 50 as illustrated in FIG. 2 which may include two thermally actuated components 10 such as those discussed above. In embodiments, as noted above, control circuitry 1010 or any other suitable control element may be provided on or operatively connected to the implant 1000 and control extension and retraction of the rod 24. In embodiments, the rod 24 may be or may be operatively connected to a brace or other corrective structure and used to make adjustments thereto in a controlled and finite manner that avoids the dangers discussed above.

In embodiments, the implant 1000 may also include one or more transceivers (transmitter/receiver) or other communication devices 1020 configured to receive control signals or other information associated with the operation of the implant 1000 and/or to transmit information regarding operation of the implant, such as the feedback position information discussed above regarding the position of the rod 24. As noted above, for example, the hydraulic system 50 may include one or more sensors to provide feedback associated with a position of the rod 24. In embodiments, this feedback information may be provided to a doctor or other healthcare professional such that proper positioning and adjustments may be provided by the implant 1000. In embodiments, a power source 1030 may be provided on the implant 1000 and operatively connected to the hydraulic system 50 as well as the control circuitry 1010 and/or the individual actuator components 10 included in the hydraulic system. In embodiments, the power source 1030 may be the secondary coil discussed above or any other inductive power source. In embodiments, the power source 1030 may be any suitable power providing element, including a battery or direct current source, for example. As noted above, the actuator components 10 may be controlled by the control circuitry 1010, for example. In embodiments, feedback information regarding the operation of the implant 1000, including the position of the rod 24 in the hydraulic system 50 may be periodically or aperiodically sent to a doctor or healthcare professional, or one or more computer systems or communication devices associated therewith. In embodiments, the doctor or healthcare professional may provide instructions associated with operation of the implant 1000 via a computer system or communication device associated therewith to the control circuitry 1010 via the transceiver 1030 to adjust the position of the rod 24.

Figure 10:
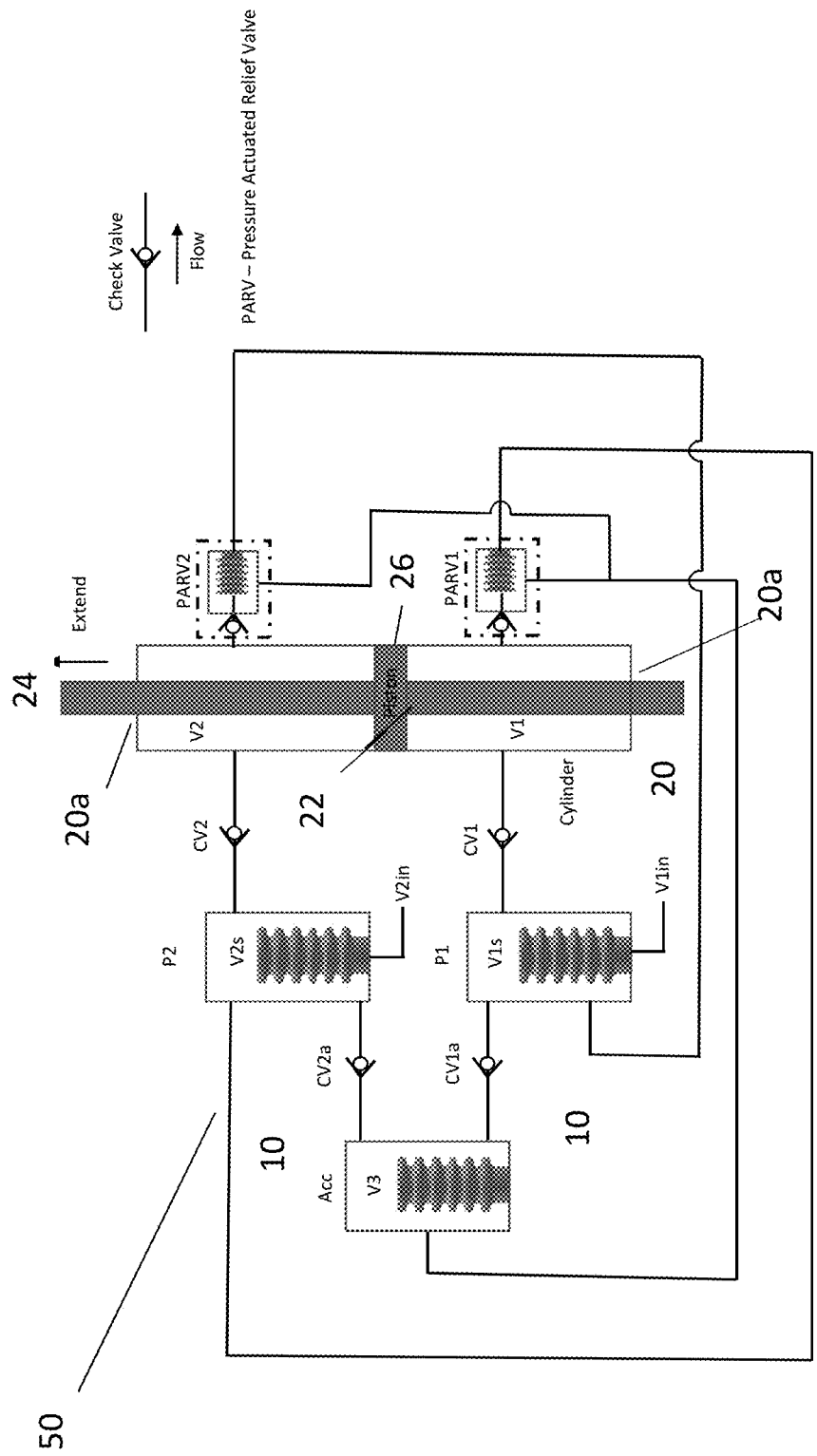
FIG. 10 illustrates a hydraulic pressure system using the component of FIG. 1 in accordance with another embodiment of the present application.

FIG. 10 illustrates an alternate embodiment of a hydraulic system 150, similar to the system 50 described above that may be used in the implant 1000. In embodiments, as in FIG. 2 the hydraulic cylinder 20 includes a piston 22 held within the closed cylinder 20. In embodiments, the piston 22 may be connected to a rod 24 that extends through both ends of the closed cylinder 20 and extends and retracts as the piston moves in the cylinder. In embodiments, a dynamic seal 26 may be provided around the periphery of the piston 22. In embodiments, additional dynamic seals may be provides around the cylindrical openings 20$a$ at the ends of the cylinder 20 through which rod 24 exits. As illustrated the cylinder 20 may be divided into two isolated volumes V1, V2 by the piston and dynamic seal 26. In embodiments, transferring fluid into one volume while removing it from the other volume will drive the piston 22 in one direction toward the volume with lower pressure along the axis of the cylinder 20 in a manner similar to that described above with respect to FIG. 2. The first volume is denoted V1 and the second volume is denoted V2. The first volume V1 and second volume V2 will increase or decrease as a function of piston translation. The total volume V1+V2 will remain more or less constant as the rod 24 extends and retracts since the rod extends into both the volume V1 and the volume V2.

In embodiments, extension of the piston 24 may be affected by the application of a voltage at the electrical input V1in. In embodiments, the voltage may be used to power the electric heater 16 discussed above, for example, causing wax to melt and resulting in expansion of the actuator 10 within volume V1$a$ to expand, thereby increasing the pressure within volume V1in. In embodiments, the voltage V1in may be used to power a controller or control circuitry that maybe use to control the heater 16. In embodiments, the voltage V1in may be applied using an inductive coupling or may be a direct source of current. In embodiments, the check valve CV1 allows fluid to flow from V1$s$ to V1 in the cylinder 20 when the pressure in V1$s$ exceeds a certain value. In embodiments, the certain value will depend on external applied loads and the cross-sectional area of the actuator for the given apparatus. In embodiments, at the same time, the increased pressure in V1$s$ is applied to the pressure relief valve PARV2 allowing fluid to flow from volume V2 to volume V3 which is designated as the accumulator. In embodiments, the increase of pressure in volume V1 as fluid flows from the volume V1$s$ into volume V1, combined with the decrease in pressure in volume V2 as fluid flows from volume V2 to volume V3 causes the piston 22 to move upward and extend the rod 24 upward. In embodiments, once the voltage V1in is removed, the wax in the actuator 10 in the volume V4 begins to contract, lowering the pressure in volume V1$s$ causing the check valve CV1 to close and the valve CV1$a$ to open allowing fluid to flow from volume V3 into volume V1$s$. Once the actuator 10 in volume V1$s$ is completely retracted to its retracted state, the pressure in volume V1$s$ returns to the value it had prior to the actuation cycle by taking up fluid from volume V3, if necessary. In embodiments, the relative volumes would be dependent on the size of the implant and the amount of extension desired for a single expansion cycle.

In embodiments, retraction of the rod 24 may be affected by the application of voltage at electrical input V2in. This voltage may be provided to induce a current in the actuator component 10 in the volume V2$s$ or may be used to provide a direct current. In embodiments, application of the voltage causes the heating element 16 in the actuator component 10 contained within volume V2$s$ to heat the wax and expand the actuator to increase the pressure within volume V2$s$. In embodiments, the check valve CV2 allows fluid to flow from volume V2$s$ to volume V2 of the cylinder 20 when the pressure in volume V2$s$ exceeds a certain value. In embodiments, the specific values are a function of the desired application and relief pressures would depend on the applied external loads. In embodiments, check valves would operate at very low differential pressures sufficient to eliminate the possibility of back flow. In embodiments, at the same time, the increased pressure in V2$s$ is applied to the pressure actuated relief valve PARV1 allowing fluid to flow from volume V1 to volume V3. In embodiments, this increase of pressure in the volume V2 and decrease of pressure in the volume V1 causes the piston 22 to move down and retract the rod 24 from the top and extent it through the bottom. In embodiments, once the voltage V2in is removed, the actuator component 10 within volume V2$s$ begins to contract back to its original state, lowering the pressure in V2$s$ causing the check valve CV2 to close and valve CV2$a$ to open allowing fluid to flow from volume V3 into volume V2$s$. In embodiments, once the actuator component 10 in volume V2$s$ is completely contracted into its original state, the pressure in volume V2$s$ returns to the value it had prior to the actuation cycle by taking up fluid from volume V3 The pressure in the various volumes is solely a function of the applied external loads.

In embodiments, either the expansion cycle or the retraction cycle described above may be repeated as many times as necessary to move the rod 24 to any incremental position. In embodiments, the size of the increment for each movement may be set based on restricting how much the component 10 expands. In embodiments, different sized or volume actuator components 10 may be used in different applications. In embodiments, Volume would be dependent on the size of the implant and the amount of extension desired for a single expansion cycle. In the embodiment of FIG. 10, since the rod 24 extends out both the bottom and the top of the cylinder 20, the rod accumulator volume Acc can be smaller that that described above with respect to FIG. 2. In the embodiment of FIG. 10, extension or retraction of the rod 24 results in substantially identical volumetric change to both volumes V1 and V2 and the accumulator Acc need only contain a single cycle of volumetric change. In embodiments, the hydraulic system 150 may be implemented in the implant 1000, discussed above in place of the hydraulic system 50. Otherwise the implant 1000 will operate in substantially the same manner as described above.

FIGS. 3-8 illustrate an embodiment of an intermedullary lengthening nail 110 that may use a bidirectional thermally actuated component 110 that operates consistent with the actuator component 10 described above. In embodiments, the implant 1000 may be the intermedullary lengthening nail 110. FIG. 3 illustrates embodiment of an intermedullary lengthening nail 110 that utilizes a mechanical extension of a thermally actuated actuator component. FIG. 4 illustrates a cross-sectional view of the an intermedullary lengthening nail 110 along the Section A-A. In embodiments, the intermedullary lengthening nail 110 extends by driving either a screw portion or a nut portion of a typical jack screw arrangement based on operation of one or more thermally actuated actuator elements that use heating elements in a manner similar to that used in the actuator component 10 discussed above. In embodiments, the drive mechanisms may be provided at opposite ends of the device 110 as shown in circles B and D of FIG. 4. Embodiments of these sections are shown in more detail in FIGS. 5 and 7. An exemplary jack screw arrangement is shown in circle C of FIG. 2 and is shown in more detail in FIG. 8.

Figure 5:
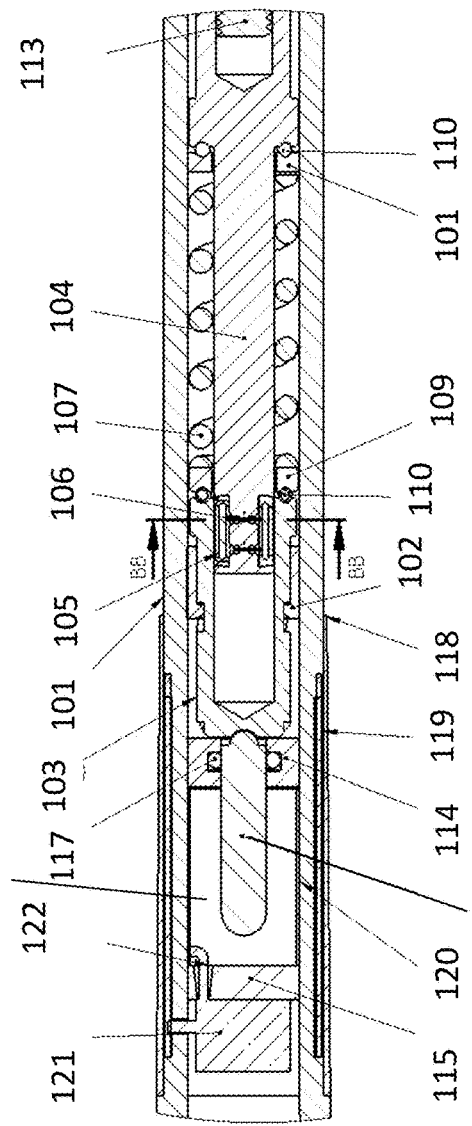
FIG. 5 illustrates a more detailed view of a drive portion of the intermedullary lengthening nail of FIG. 4.
Figure 7:
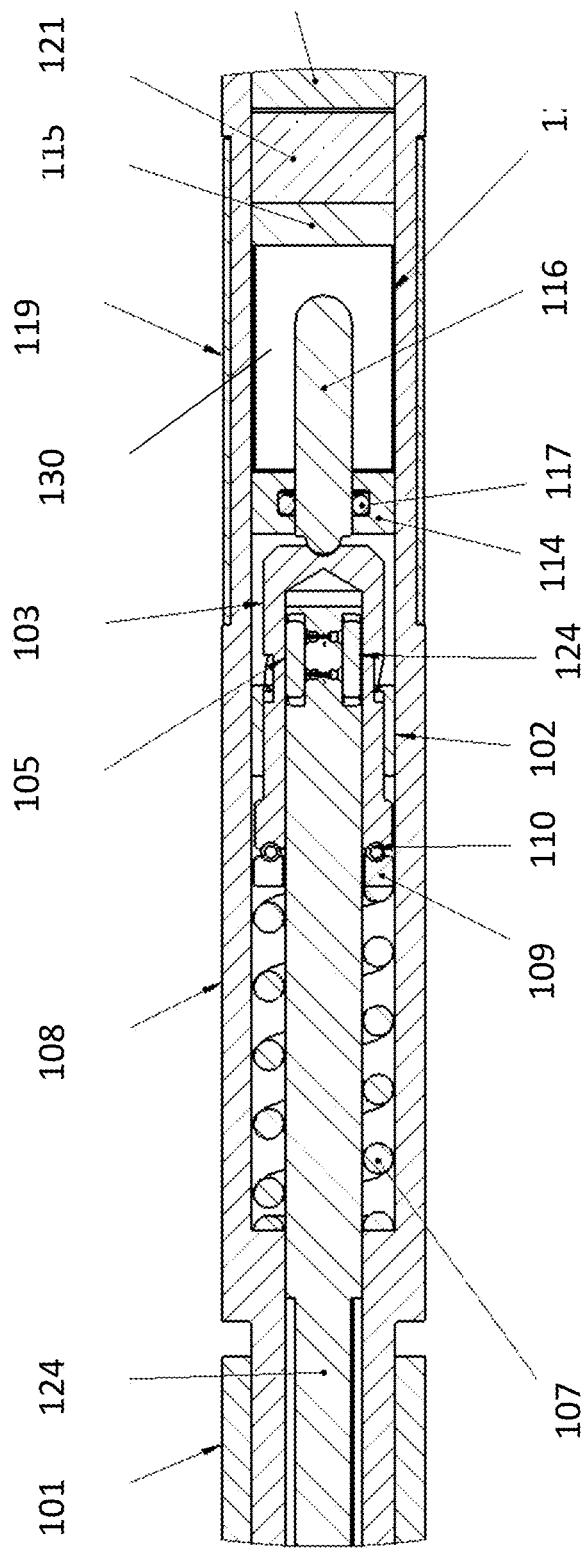
FIG. 7 illustrates a more detailed view of another drive portion of the intermedullary lengthening nail of FIG. 4.

In embodiments, the drive portions highlighted in circles B and D in FIG. 3 and illustrated in more detail in FIGS. 5 and 7 may include a body 101 which includes an inductive pickup coil 119, under a cover item 118. In embodiments, this inductive pickup coil 119 may be the power source 1030 discussed above. In embodiments, when an external fluctuating electromagnetic field is brought into proximity of the pickup coil 119 a current may induced within the pickup coil. In embodiments, the external fluctuating electromagnetic field may be provided via a primary coil, as discussed above and may be provided outside of a user's body in which the IM nail 110 may be implanted. In embodiments, the current may be applied to internal control electronics 121, which may be or include the control circuitry 1010 discussed above. In embodiments, the control electronics 121 may be used to power on and off a heating element 120. In embodiments, the heating element 120 surrounds a eutectic wax material 130 trapped between bulkheads 114 and 115. The heating element 120 may be a resistive heating element similar to heating element 116 discussed above or any other suitable heating device. In embodiments, a piston 116 may be encased within the wax material 130 and exit through the bulkhead 114. In embodiments, a seal 117 may keep the wax material 130 from escaping the enclosed volume between the bulkheads 114, 115 and allow the piston 116 to travel in and out of the enclosed volume. In embodiments, when the heating element 120 heats the wax material 130, the wax melts and expands generating an internal pressure on the order of 3000 psi. In embodiments, the expansion of the wax forces the piston 116 to extend through the bulkhead 114 to bear on a male helical spline 103. In embodiments, the spline 103 slides within a female helical spline 102 which is fixed to the body 101. In embodiments, the helical nature of the spline 103 results in the rotation of spline as it is forced by the piston 116 to move in a linear fashion. In embodiments, this rotation operates a roller clutch shown in FIG. 6. In embodiments, the roller clutch may include a bore within the spline 103 that has a shaft 104 positioned inside it. In embodiments, the shaft 104 may include an array of rollers 105 in slanted slots machined into the shaft. In embodiments, the rollers 105 are biased to the narrow side of the slanted slots using wire spring 104a. In embodiments, the clutch drives rotation of the shaft 104 in lockstep with the driving spline 103, when it is rotating in the counterclockwise direction. In embodiments, this rotation takes place while the piston 116 is extending. That is, the linear extension of the piston is translated into rotation.

In embodiments, when the piston 116 is retracting, the spline 103 rotates in the clockwise direction. In embodiments, when this happens, the shaft 104 is no longer engaged with spline 103. In embodiments, the shaft 104 drives an integral nut 111 (see FIG. 8). In embodiments, counterclockwise rotation of the nut 111 causes extension of rod 113. In embodiments, to return the piston 116, and the male helical spline 103 to the original state, a return spring 107 is utilized. In embodiments, the return spring 107 operates between a bulkhead 112 (see FIG. 8) and the piston 116. In embodiments, the bulkhead 112 is fixed to the body 101. In embodiments, the return spring 107 applies force through a thrust bearing 109, 110 such that the male spline 103 is free to rotate as it linearly moves back and forth.

Figure 8:
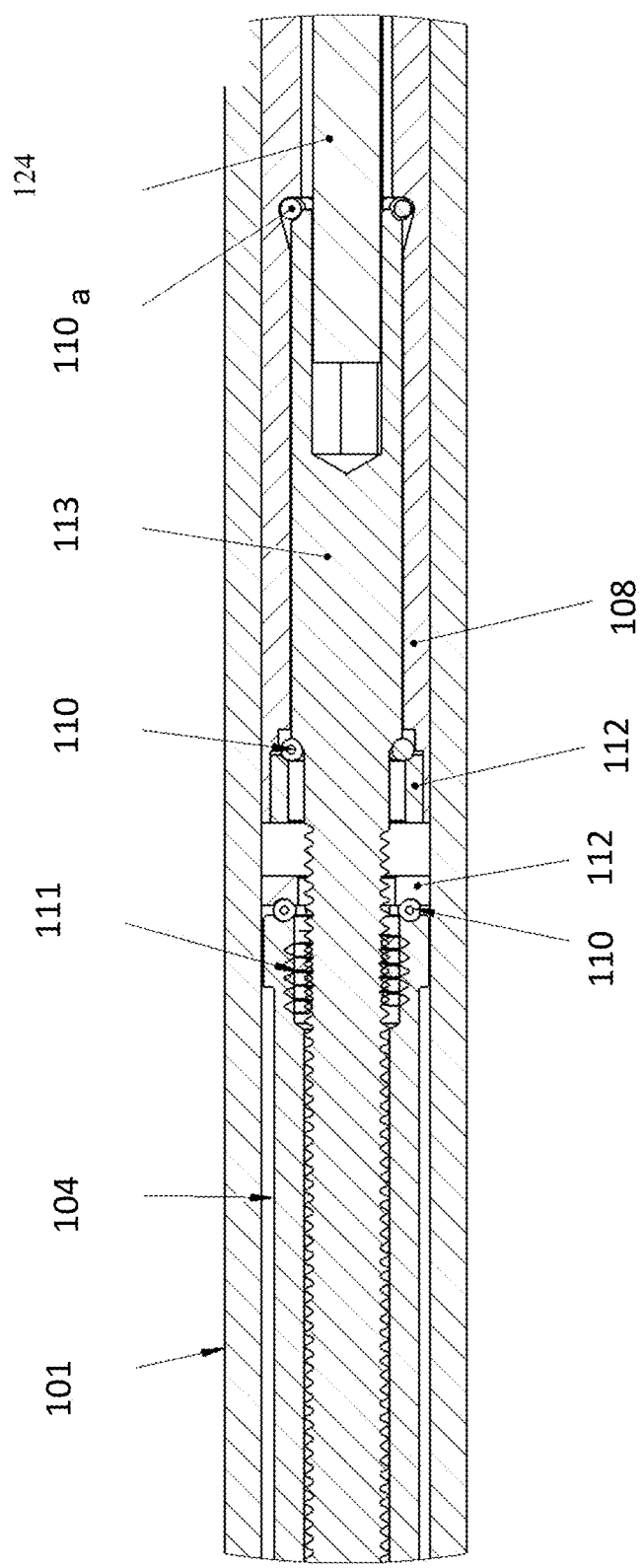
FIG. 8 illustrates a more detailed view of a jackscrew portion of the intermedullary lengthening nail of FIG. 4.
Figure 9:
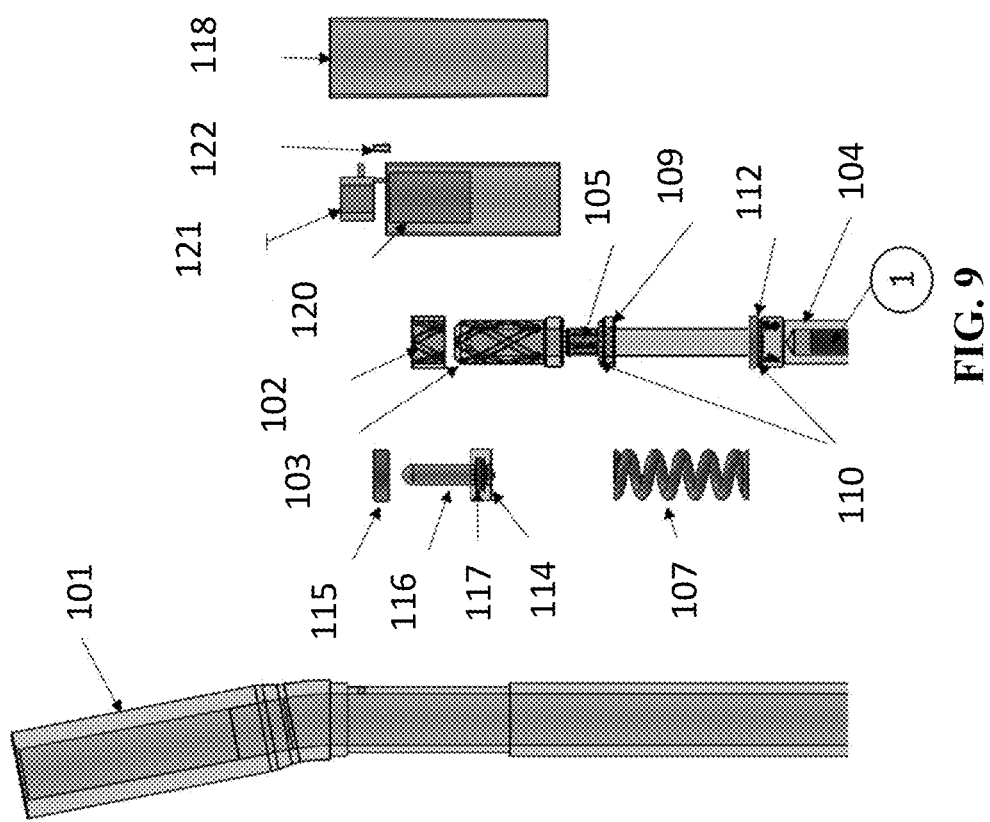
FIG. 9 illustrates an exploded view of the drive portion of FIG. 6.

In embodiments, the jack screw mechanism which can be seen in more detail in FIG. 8 includes the shaft 104, the nut 111 and the jack screw 113. In embodiments, the shaft 104 may be supported between a pair of thrust bearings 110a which are fixed to the body 101. In embodiments, the jack screw 113 is linearly fixed but free to rotate with respect to the nail rod 108. In embodiments, additional bearings 110a may be captured between items 108 and 113 to provide for rotation. In embodiments, a bearing race 123 may be fixed to the nail rod 108. The bullet tip 126 of the nail 110 can be seen in FIG. 7a. In embodiments, the bullet tip 126 may be a static part and may be attached to the shaft 108. As can be seen with reference to FIG. 7, for example, the drive mechanism highlighted in the circle D and shown in detail in FIG. 7 has a similar structure and operation as that shown in FIG. 5 except that the piston 116 moves in the opposite direction.

Figure 4A:
FIG. 4A illustrates an exemplary embodiment of the intermedullary lengthening nail of FIG. 3 in an expanded position.
Figure 6:
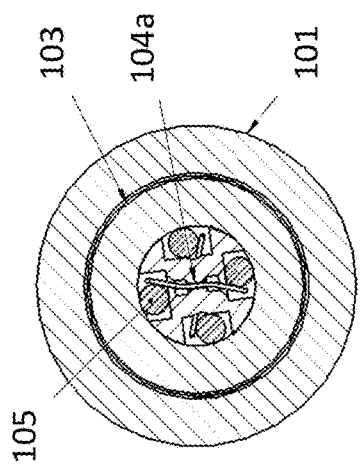
FIG. 6 illustrates a cross sectional view of the drive portion of the intermedullary lengthening nail of FIG. 5.

In operation, the intermedullary lengthening nail 110 may either extend or retract. In order to extend, in embodiments, the mechanism illustrated in in circle B and FIG. 5 provides counterclockwise rotation of the shaft 104 relative to the jack screw 113 which causes the jackscrew to extend out of the shaft in accordance with the thread pitch of the nut 111. In order to retract, in embodiments, the mechanism described in circle D and FIG. 7 provides clockwise rotation of the jackscrew 113 relative to the shaft 104 which causes the jackscrew to retract within the shaft 4 in accordance with the thread pitch of nut 111. FIG. 4A illustrates the intermedullary lengthening nail 110 in an extended position.

In embodiments, power and data communication may be provided to/from the implant 1000, which may be embodied by the intermedullary lengthening nail 110. In embodiments, the direct communication may be provided via a direct connection to a mobile phone, via the transceiver 1020, for example. In embodiments, the direct connection may be provided utilizing a charging cable, USB cable or other wired connection. In embodiments, the charging cable may be used both to provide power and capture or communicate positional data regarding the operation of the piston 124, for example. In embodiments, power maybe provided based on induction using a near field inductive coupling as generally discussed above with respect to the power source 1030. In embodiments, commands may be transmitted and positional data exchanged via the inductive coupling as well. In embodiments, this information may be transmitted wirelessly via the transceiver 1020.

In embodiments, the internal control electronics 121, which may correspond to the control circuitry 1010 discussed above, may be used to communicate positional information either directly or via inductive coupling. In embodiments, the control electronics 121 may include one or more processors or microprocessors or other control circuitry. In embodiments, the control electronics 121 may include or be connected to a port or plug to allow for direct connection to a mobile phone or other mobile device. In embodiments, the control electronics 1020 may include a transceiver, such as transceiver 1020 discussed above, to send and receive information wirelessly. In embodiments, as noted above, communication may be accomplished via inductive coupling. In embodiments, wireless communication may take place using any suitable wireless protocol or network which may be implemented via the transceiver 1020, for example.

Figure 11:
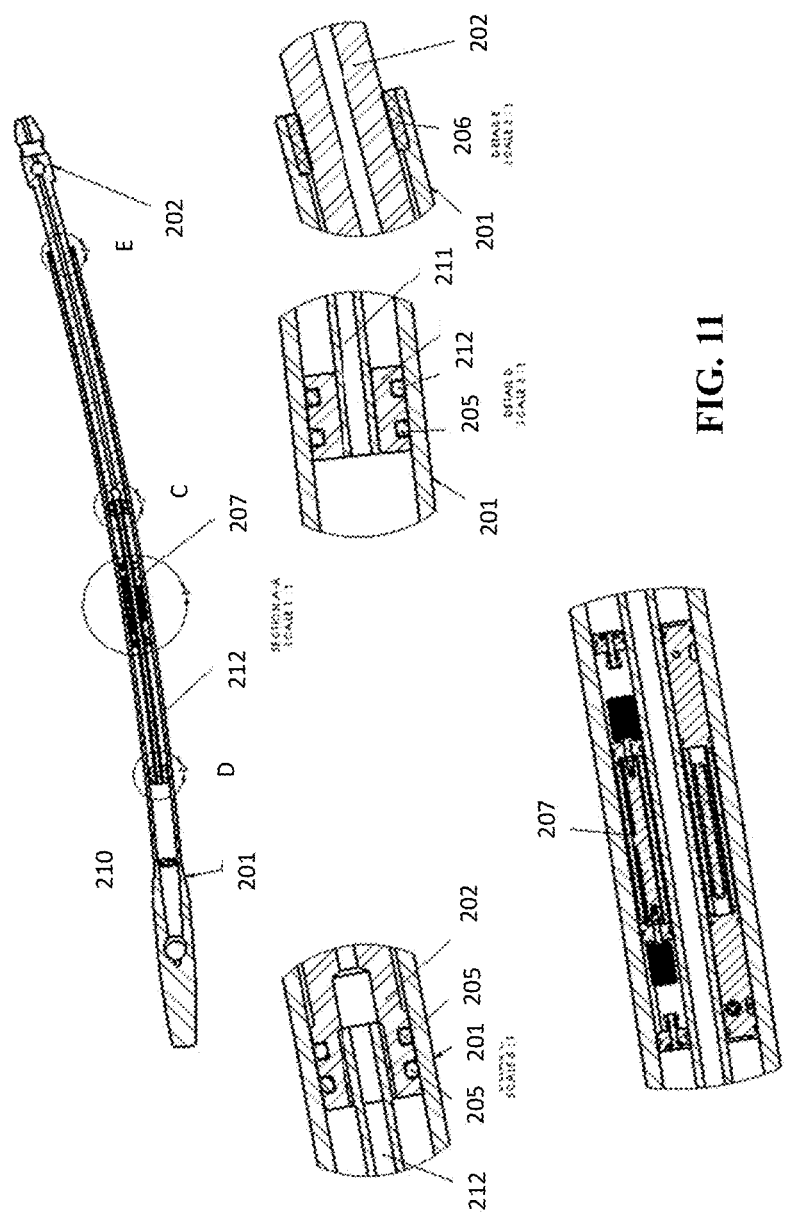
FIG. 11 illustrates a bidirectional thermally actuated component in accordance with another embodiment of the present application.

FIG. 11 illustrates another embodiment of an intermedullary (IM) lengthening nail 210 that uses a bidirectional thermally actuated component similar to the actuator component 10 discussed above. In embodiments, a nail body 201 may be the main structural element of the IM nail 210 and may be hollow to accommodate a nail shaft 202, which is slidably engaged in the body and sealed by a pair of O-rings 205. In embodiments, other seal structures may be used in place of the O-rings. In embodiments, the body 201 and the shaft 202 may share a common curvature and may be configured to avoid rotation using a bushing 206. In embodiments, the body 201 and the shaft 202 may have a substantially cylindrical shape. In embodiments, a bidirectional pump element 207 may be provided in the nail body 201 and fixed to prevent movement of the pump relative to the body 201. In embodiments, a seal 209 may be provided to prevent fluid from passing between the first volume V1 and the second volume V2. In embodiments, the seal 209 (see FIG. 14) may be a static seal and may be used to prevent this fluid transfer. In embodiments, a tension rod 211 may be engaged with the nail shaft 202 and may continue through the pump 207 and connect to a piston 211 which may be sealed by the O-rings 205.

Figure 12:
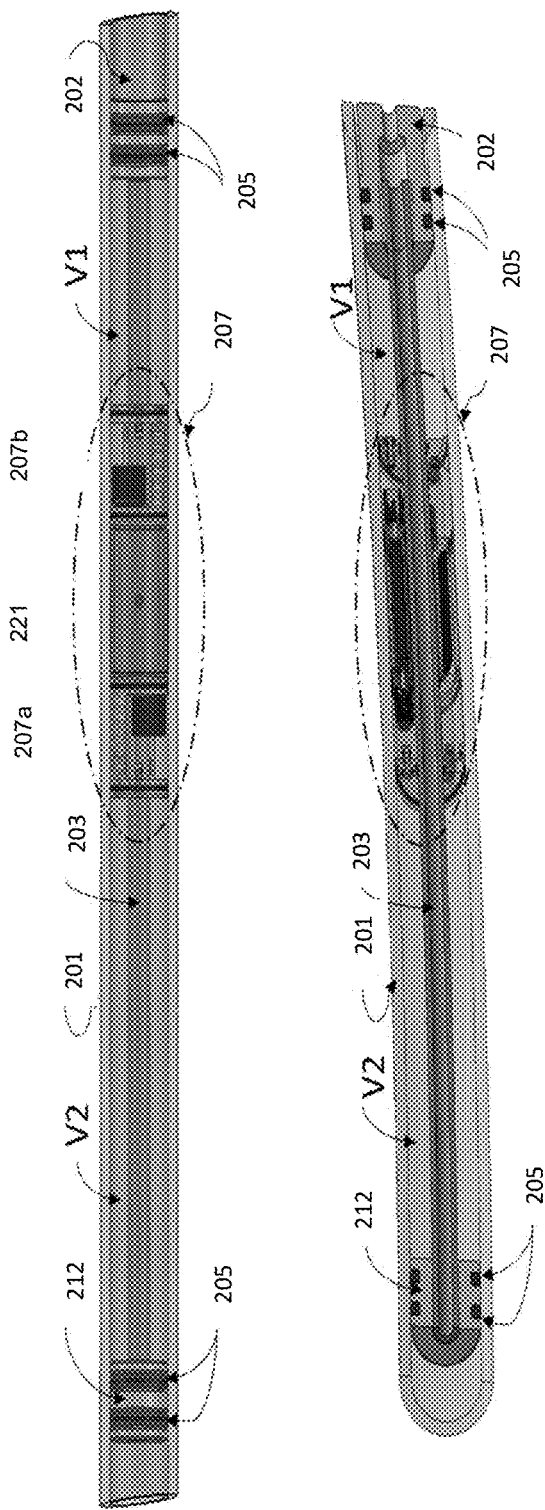
FIG. 12 illustrates a partially transparent view of the intermedullary lengthening nail of FIG. 11 showing a bidirectional pump included therein.

FIG. 12 illustrates the pump 207 and the cylinder volumes V1, V2 that are included in the nail body 201. In embodiments, the pump 207 may be positioned in the body 201 with the tension rod 211 extending through the pump 207 as noted above. The volume V1 may be provided in the space between the pump 207 and the nail shaft 202. The volume V2 may be provided between the pump 207 and the piston 212. In embodiments, the pump 207 may move fluid from the volume V1 to the volume V2 in order to retract the piston 212. The pump 207 may also move fluid from the volume V2 to the volume V1 to extend the rod 211. In embodiments, a cannula 203 in the rod extends through the tension rod 211 which is slidably engaged in shaft 202. In embodiments, the cannula 203 may be used to facilitate insertion over a guide wire which is a common technique used for implanting IM nails in a patient's body. In embodiments, the IM nail 210 may be an example of an implant 1000 discussed above.

Figure 14:
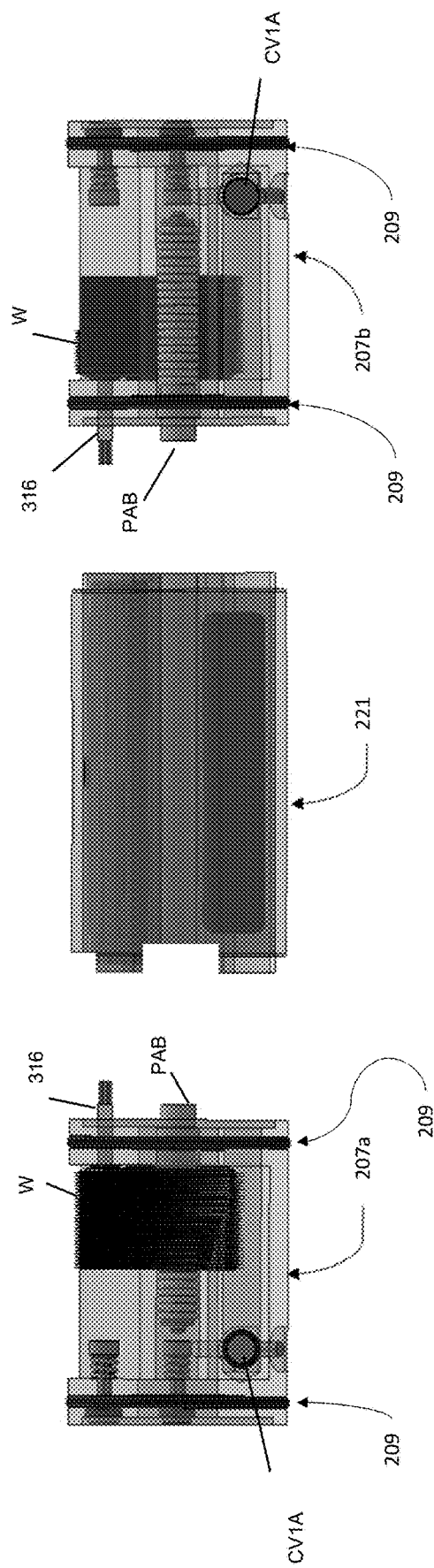
FIG. 14 illustrates a partially transparent view of the intermedullary lengthening nail of FIG. 12.

FIGS. 13-14 illustrate components of the bidirectional pump 207. In embodiments, the pump 207 may include three main parts. An interstage section 221 may include power, electronics and an accumulator volume. In embodiments, a pair of thermal pump mechanisms 207a, 207b may be provided at either end of the interstage section 221. In embodiments, the pump mechanisms 207a, 207b may be used to force fluid from the pump 207 into the volumes V1, V2 to effect extension and retraction. In embodiments, the hydraulic working fluid may be, among other substances, sterile water isolated from an encapsulated thermal wax actuator in the pump mechanisms 207a, 207b and may be contained within the cylinder volumes V1, V2. In embodiments, the application of voltage V1in or voltage V2in energizes a heating element, such as the heating element 16 discussed above within the wax actuator used in the pump mechanisms 207a, 207b resulting in a phase change from solid to liquid and associated expansion of the wax actuator. In embodiments, this expansion of the thermally actuated actuator similar to the actuator component 10 discussed above, may displace and pressurize the working fluid resulting in an increase of working fluid pressure within the pump 207.

Figure 15:
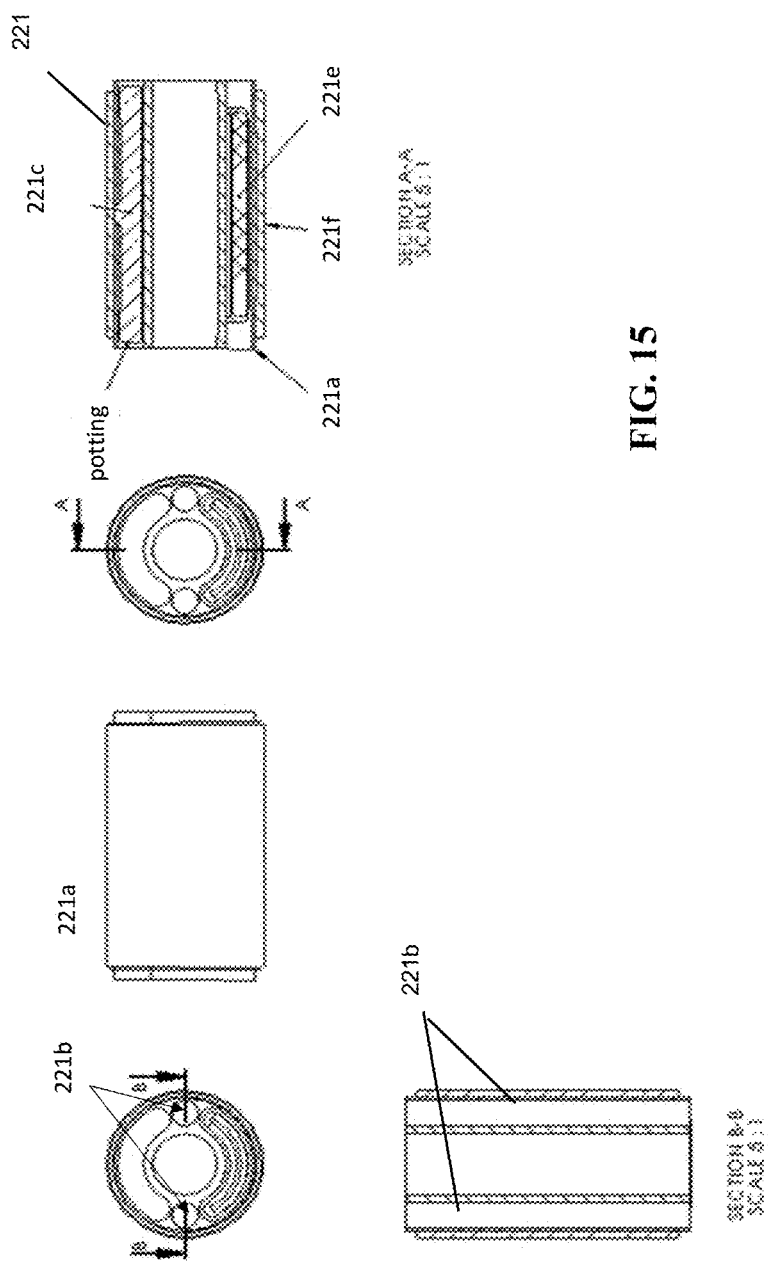
FIG. 15 illustrates a detailed view of an interstage section of the intermedullary lengthening nail of FIG. 12.
Figure 16:
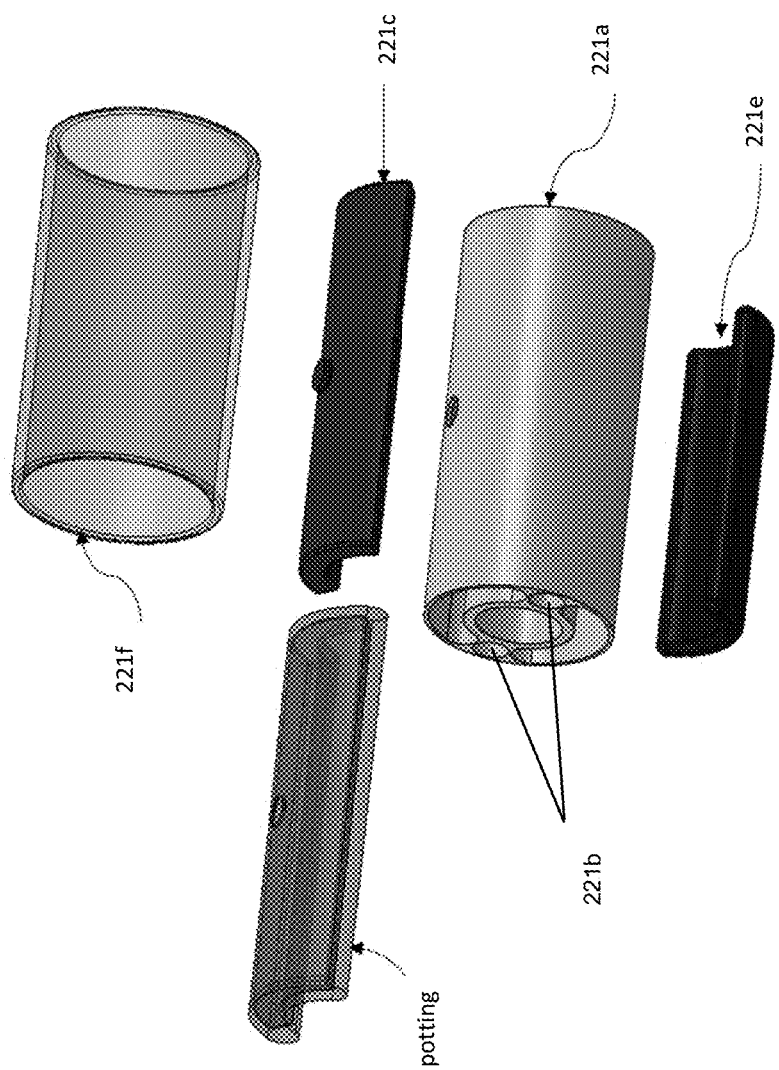
FIG. 16 illustrates an exploded view of the interstage section of the intermedullary lengthening nail of FIG. 12.

FIGS. 15-16 illustrate cross-sectional and exploded views, respectively, of the interstage section 221. An interstage body 221a may serve as a housing for the remaining components. In embodiments, a pair of fluid passages 221b may be provided in the housing 221a. In embodiments, electronics 221c may be potted within a cavity and isolated from the working fluid. In embodiments the electronics 221c may include the control circuitry 1010 discuss above as well as the transceiver 1030, for example. In embodiments, a bladder 221e may be provided in a second cavity and may serve as an accumulator to accommodate displacement of fluid from the shrinking volumes V1, V2 as fluid is transferred between them. In embodiments, when one volume V1 reduces volume, the other volume V2 will experience a corresponding increase in volume which effects motion of the nail shaft 202. In embodiments, a coil 221f may be provided around the body 221a. In embodiments, the coil 221f may be a coil of wire and function as an inductive pickup to supply power to the electronics 221c. In embodiments, the coil 221f may be the power supply 1030 discussed above. In embodiments, the coil 221f may be the secondary coil discussed above. In embodiments, the electronics 221c may control operation of the pump 207 and send signals to an external controller or computer device associated with a doctor, health care professional or administrator (not shown). In embodiments, near field wireless charging and communication protocols such as Bluetooth may be used to provide power and for communication using the power source 1030 and transceiver 1020 discussed above, for example which may be incorporated into the electronics 221c. In embodiments, the ability to communicate to an external controller allows information such as positional feedback, load sensing, pressure and temperature sensing to be exported and monitored.

Figure 17:
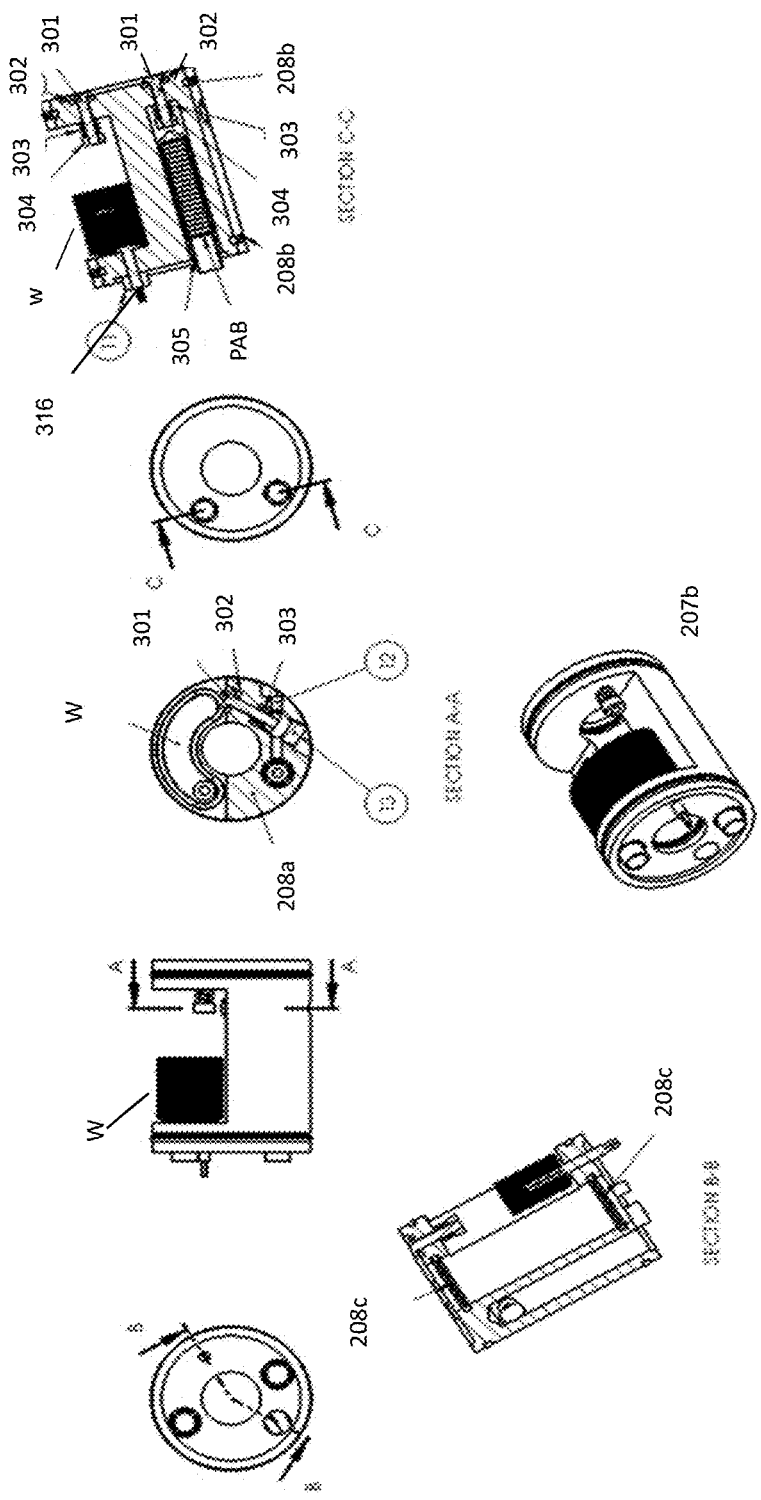
FIG. 17 illustrates a detailed view of a pump mechanism used in the intermedullary lengthening nail of FIG. 12.
Figure 18:
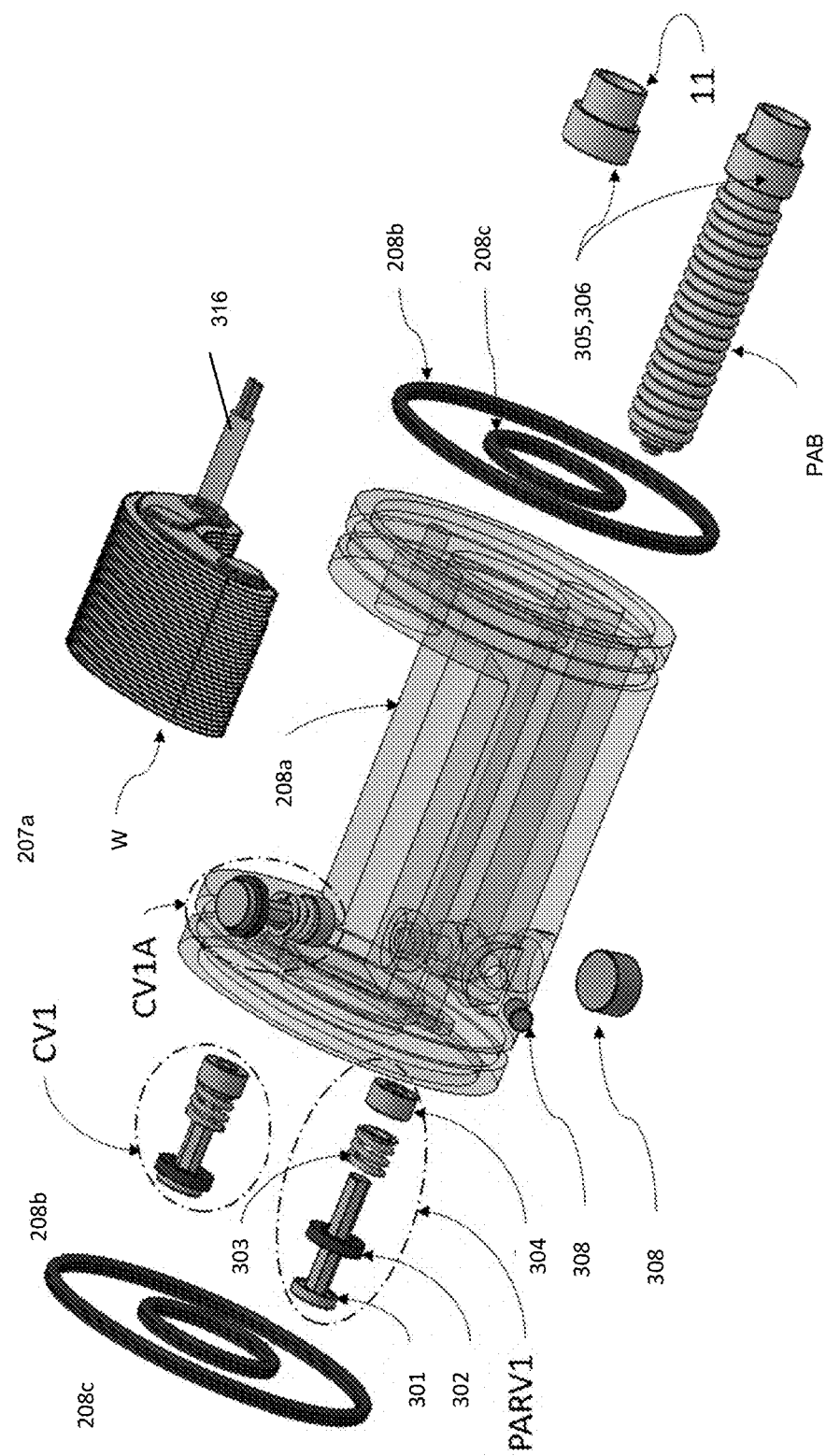
FIG. 18 illustrates an exploded view of the pump mechanism of FIG. 17.

FIGS. 17-18 illustrate cross-sectional and exploded views, respectively, of the pump mechanisms 207a, 207b. In embodiments, a body 208a houses the remaining components and allows isolation of the fluid passages between the retraction and extension pump mechanisms. In embodiments, static O-rings 208b may isolate the internal volume of the pump 207a, 207b from the cylinder volumes V1, V2. In embodiments, dynamic O-rings 208c may provide a dynamic seal between the pump mechanism 207a, 207b and the tension rod 212. In embodiments, the tension rod 212 may be allowed to completely traverse the pump assembly 207 between the cylinder volumes V1, V2 such that the need for a rod accumulator may be eliminated. In embodiments, each pump mechanism 207a, 207b may include a wax capsule or bellows W, enclosed within the working fluid volume. In embodiments, the capsule W may be the bellows 12 discussed above with the shape thereof adjusted to conform to the curvature of the body 201. In embodiments, a pair of check valves CV1, CV2, may include a poppet 301, a seat 302, a spring 303 and a stop 304, may be used to control flow into and out of the pump mechanism 207a, 207b during periods of wax capsule or bellows W expansion and retraction. In embodiments, the spring 303 may bias the poppet 301 against the seat 302 effecting a fluid seal. In embodiments, one of the check valves, CV1, may allow fluid from the pump 207 to flow into the associated cylinder volume V1, V2 when the pump is undergoing a positive expansion of the wax capsule W while the second check valve, CV12, allows flow to enter the pump from the bladder 221f provided in the interstage section 221 during a period of retraction of the wax capsule W. In embodiments, a pressure actuated relief valve, PARV1, may be constructed in a manner similar to that of the valves discussed above and includes a pressure actuated bellows PAB. In embodiments, the bellows PAB allows for an internal pressure to be communicated across the interstage section 221 from the opposing pump volume. In embodiments, the valve PARV1 allows fluid from the cylinder volume V1 or V2 whose volume is decreasing to flow into the bladder 221e such that the respective cylinder volume V1 or volume V2 whose volume is increasing has room to extend into the accommodation provided by the bladder. In embodiments, various bushings 305 and 306 serve to connect each of the pump mechanisms 207a, 207b to the interstage section 221. In embodiments, plugs 308 may be provided to seal flow passages temporarily to allow for manufacture and assembly of the pump components. In embodiments, the check valves, CV1, CV1a, and the pressure relief valve, PARV1 may be configured differently, if desired. In embodiments, the check valves, CV1, CV1a, and the pressure relief valve, PARV1 may be magnetic bias valves, flapper valves or any other mechanical apparatus that provides for flow control.

Figure 19:
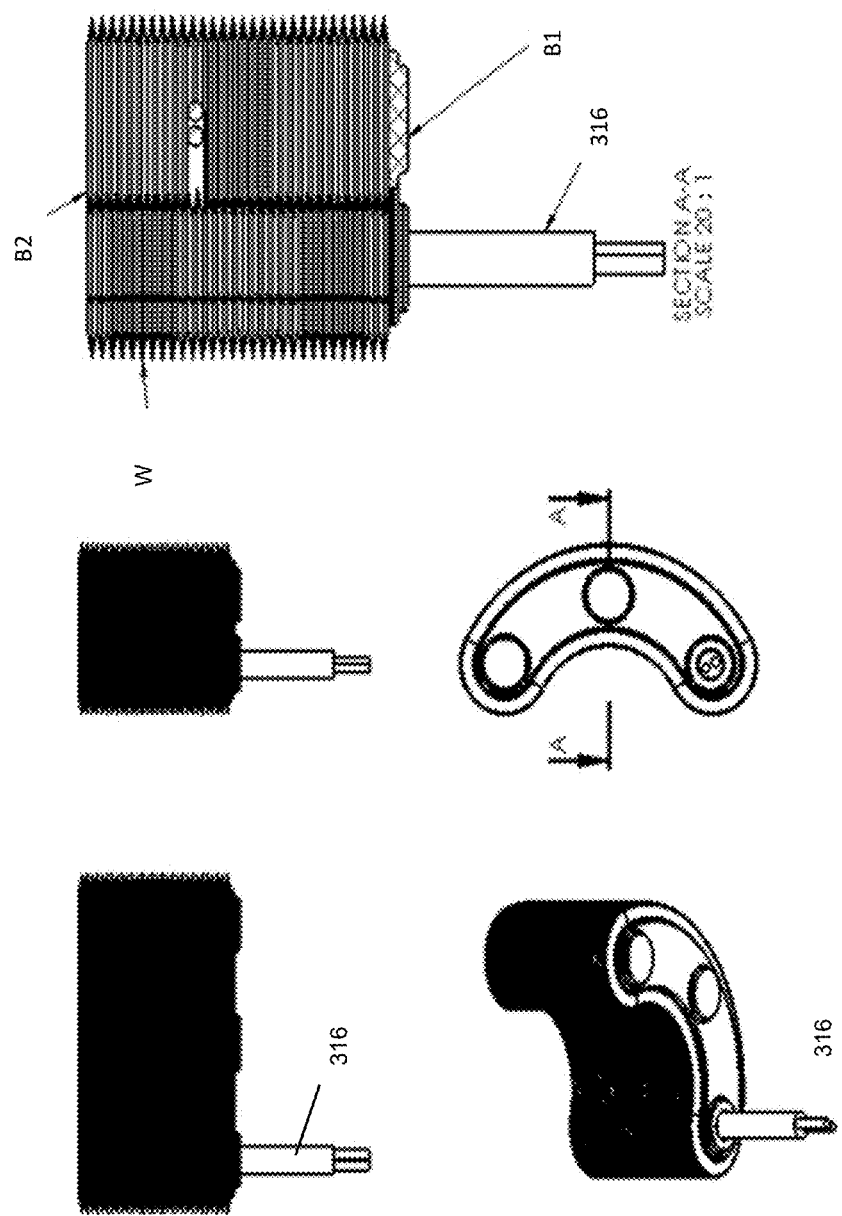
FIG. 19 illustrates a detailed view of a wax capsule of the pump mechanism of FIGS. 17-18.

FIG. 19 illustrates a detailed view of a bellows B which may be used as the wax capsule W discussed above in which a paraffin wax formulated to melt at the appropriate temperature is provided. As noted above, the capsule W may be the bellows 12 discussed above. In embodiments, a heating element 316 may provide the energy input to melt the wax and may be controlled by the electronics 221c. In embodiments, the wax undergoes a volumetric expansion of up to 20% during melting. In embodiments, the pressure generated during this expansion, when properly constrained, approaches 3000 psi. As illustrated in FIG. 18, the bellows B is shown as a typical edge welded bellows assembly however other structures for wax encapsulation may be used, such as a silicone bladder or a piston in a cylinder to name a few. In embodiments encapsulation of the wax isolates it from the working fluid and maintains its proximity to the heating element 316. The heating element 316 may be similar to the heating element 16 discussed above. In embodiments, once power is removed from the heating element 316, the wax dissipates the heat to the working fluid and solidifies causing retraction of the bellows. In embodiments, the bellows B may include two opposed endcaps B1, B2 with a flexible segmented diaphragm D positioned therebetween to expand and contract as the wax melts and solidifies. In embodiments, other flexible structures may be used as the bellows B.

Figure 20:
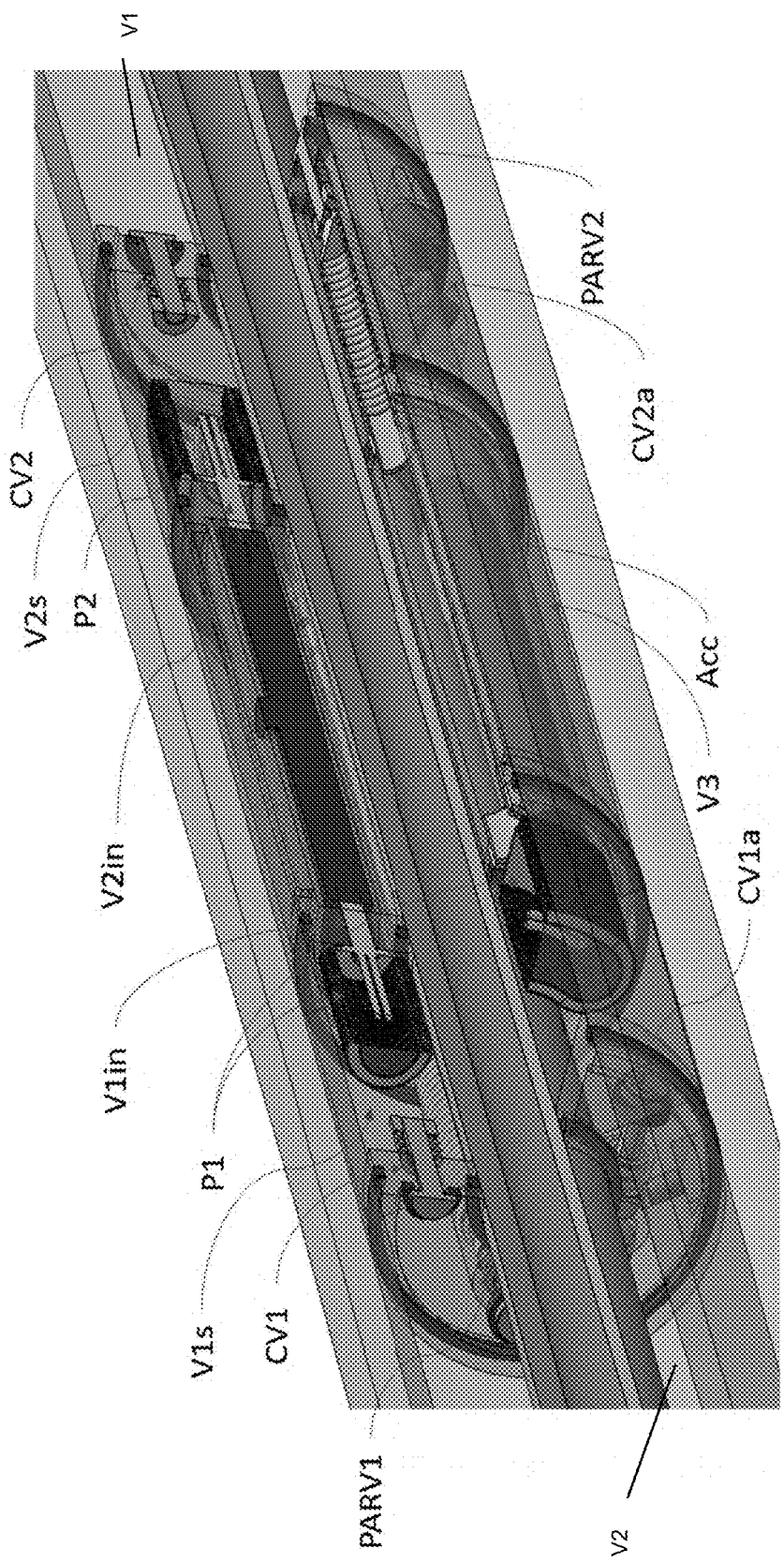
FIG. 20 illustrates a partially transparent view of the bidirectional thermally actuated component of FIG. 11.

FIG. 20 illustrates the hydraulic pump section 207 with a portion thereof cut away. In embodiments, a piston 212 may be held within a closed cylinder 201 (see FIG. 12). In embodiments, in order to effect motion outside of the cylinder, the piston may be connected to a rod that extends through the end of each of the closed cylinder volumes V1, V2. In embodiments, a dynamic seal is provided around the periphery of the piston and around the cylindrical opening at the ends of the cylinder volume V1, V2 through which the rod R exits to divide the cylinder C into two isolated cylinder volumes V1 and V2. In embodiments, transferring working fluid into one volume V1, V2 while removing it from the other volume will drive the piston P in one direction along the axis of the cylinder C. In embodiments, the first volume denoted V1 and the second volume denoted V2 will increase or decrease as a function of piston translation. In embodiments, the use of such an actuator in a closed fluidic cycle includes a third connected variable volume V3 to accommodate the fluid flowing out of the decreasing volume during the time at which fluid is being pumped into the volume that is increasing. This third volume Acc is referred to as an accumulator and may be constructed using a spring-loaded piston in a cylinder, a flexible bellows, or a gas filled bladder, to name a few, in an enclosed volume as has been depicted. In embodiments the second function of this accumulator Acc may be to resupply the pump 207 during a period where the wax capsule is cooling and decreasing in volume, thus drawing fluid in from the Acc allowing the pump to be primed for the next actuation cycle.

Now that embodiments of the present invention have been shown and described in detail, various modifications and improvements thereon can become readily apparent to those skilled in the art. Accordingly, the exemplary embodiments of the present invention, as set forth above, are intended to be illustrative, not limiting. The spirit and scope of the present invention is to be construed broadly.

What is claimed is:

1. A thermally actuated component comprises:
   a flexible container element expandable into an expanded state and biased to return to a retracted state;
   a thermally responsive material stored in the flexible container; and
   a heating element positioned such that heat from the heating element melts the thermally responsive material when the heating element is activated such that the flexible container expands into the expanded state and the thermally responsive material contracts as it cools when the heating element is deactivated such that the flexible container returns to the retracted state.

2. A thermally actuated component comprising:
   a first volume filled with a working fluid;
   a first actuator mounted in the first volume, the first actuator including a flexible element configured to selectively expand when the first actuator is activated;
   a cylinder in fluid communication with the first actuator and filled with the working fluid;
   the cylinder including:
      a second volume positioned on a first end thereof and in fluid communication with the first volume; and
      a third volume position on a second end thereof; and
   a piston mounted in the cylinder between the second volume and the third volume and movable between a first position and a second position based on working fluid pressure in the second volume and the third volume such that the piston moves from the first position to the second position when the flexible element of the first actuator expands to increase a first pressure in the first volume and force working fluid into the second volume to apply pressure to the piston toward the second position; and
   an accumulator volume in fluid communication with the second volume and the third volume to receive working fluid as the piston moves between the first position and the second position.

3. The thermally actuated component of claim 2, further comprising a first check valve positioned between the first volume and the second volume to control fluid flow from the first volume to the second volume.

4. The thermally actuated component of claim 3, further comprising a first pressure responsive valve positioned between the third volume and the accumulator volume and configured to selectively open to allow working fluid to flow from the third volume to the accumulator volume as the piston moves when the pressure in the first volume exceeds a threshold.

5. The thermally actuated component of claim 4, wherein the accumulator volume is in fluid communication with the first volume and provides working fluid to the first volume when the first actuator is deactivated and the flexible element contracts.

6. The thermally actuated component of claim 5, further comprising a second check valve positioned to control flow of working fluid from the accumulator volume to the first volume.

7. The thermally actuated component of claim 6, further comprising:
a fourth volume including the working fluid and in fluid communication with the third volume of the cylinder;
a second actuator mounted in the fourth volume, the second actuator including a flexible element configured to selectively expand when the second actuator is activated;
wherein the piston is movable from the second position to the first position based on working fluid pressure in the second volume and the third volume such that the piston moves in a second direction, opposite the first direction, when the flexible element of the second actuator expands to increase a second pressure in the fourth volume and force working fluid into the third volume to apply pressure to the piston in the second direction.

8. The thermally actuated component of claim 7, further comprising a third check valve positioned between the fourth volume and the third volume to control working fluid flow from the fourth volume to the third volume.

9. The thermally actuated component of claim 8, wherein the accumulator volume receives working fluid from the second volume as the piston moves from the second position to the first position.

10. The thermally actuated component of claim 9, further comprising a second pressure responsive valve positioned between the second volume and the accumulator volume and configured to selectively open to allow working fluid to flow from the second volume to the accumulator volume as the piston moves from the second position to the first position when the pressure in the fourth volume exceeds a second threshold.

11. The thermally actuated component of claim 9, wherein the accumulator volume is in fluid communication with the fourth volume and selectively provides working fluid to the fourth volume when the second actuator is deactivated.

12. The thermally actuated component of claim 11, further comprising a fourth check valve to control flow of working fluid from the accumulator volume to the fourth volume.

13. The thermally actuated component of claim 12, further comprising a rod element extending from a first side of the piston through the third volume and to a first end of the cylinder, the rod element movable with the piston such that the rod element is retracted in the cylinder when the piston is in the first position and extends out of the cylinder when the piston is in the second position.

14. The thermally actuated component of claim 13, further comprising a dynamic seal provided between the first end of the rod element and the first end of the cylinder to prevent working fluid from leaking out of the third volume.

15. The thermally actuated component of claim 14, wherein the accumulator volume is configured to accommodate a rod volume of working fluid based on dimensions of the rod element.

16. The thermally actuated component of claim 15, wherein the accumulator volume is an elastic bladder.

17. The thermally actuated component of claim 7, further comprising a second input voltage terminal configured for connection to a second voltage source and electrically connected to the third actuator, wherein the second actuator includes an electric heating element configured to produce heat to expand the flexible member of the second actuator when connected to the second voltage source.

18. The thermally actuated component of claim 17, wherein the second input voltage terminal is configured for wireless connection to the second voltage source.

19. The thermally actuated component of claim 7, further comprising:
a first coil electrically connected to the first actuator, where the first coil is configured for inductive coupling with another coil to provide power to the first actuator when the another coil is energized;
a second coil electrically connected to the second actuator, wherein the second coil is configured for inductive coupling to the another coil to provide power to the second actuator when the another coil is energized;
wherein the first coil and second coil are configured such that inductive coupling occurs based on a relative position of the first coil, the second coil and the another coil.

20. The thermally actuated component of claim 19, wherein inductive coupling is selectively provided in one of the first coil and the second coil based on the relative position of the another coil while inductive coupling does not occur in the other of the first coil and the second coil.

21. The thermally actuated component of claim 2, further comprising a first input voltage terminal configured for connection to a first voltage source and electrically connected to the first actuator, wherein the first actuator includes an electric heating element configured to produce heat to expand the flexible member of the first actuator when connected to the first voltage source.

22. The thermally actuated component of claim 21, wherein the first input voltage terminal is configured for wireless connection to the first voltage source.

23. The thermally actuated component of claim 2, further comprising a first coil electrically connected to the first actuator, where the first coil is configured for inductive coupling with a second coil to provide power to the first actuator when the second coil is energized.

24. The thermally actuated component of claim 2, further comprising a transceiver configured to send and receive data.

25. The thermally actuated component of claim 24, further comprising a controller connected to the transceiver and operable to control the first actuator and the second actuator based on instruction date received by the transceiver.

* * * * *